United States Patent
Ratcliff et al.

(10) Patent No.: US 6,369,296 B1
(45) Date of Patent: Apr. 9, 2002

(54) RECOMBINANT PLANT VIRAL VECTORS

(75) Inventors: Frank Giles Ratcliff; Ana Montserrat Martin-Hernandez; David Charles Baulcombe, all of Norwich (GB)

(73) Assignee: Plant Bioscience Limited, Norfolk (GB)

(*) Notice: Subject to any disclaimer, the term of this patent is extended or adjusted under 35 U.S.C. 154(b) by 0 days.

(21) Appl. No.: 09/495,797

(22) Filed: Feb. 1, 2000

(51) Int. Cl.[7] .......................... A01H 1/00; C12N 15/00; A01N 63/00; A01N 43/04; A61K 48/00

(52) U.S. Cl. .................. 800/278; 800/280; 800/288; 435/320.1; 424/93.21; 514/44

(58) Field of Search ................................. 800/295, 278, 800/280, 288, 297; 536/23.1, 24.1; 435/320.1; 424/93.21; 514/44

(56) References Cited

PUBLICATIONS

Marathe et al (2000) Plant Molecular Biology 43:295–306.*
Ratcliff et al (The Plant Journal (2001) 25:237–245).*
W.D.O. Hamilton et al., "The Complete Nucleotide Sequence of Tobacco Rattle Virus RNA–1"; J. gen. Virol. (1987), 68, 2563–2575.
Susanne Kjemtrup et al., "Gene silencing from plant DNA carried by a Geminivirus"; The Plant Journal (1998) 14(1), 91–100.
M.H. Kumagai et al., "Cytoplasmic inhibition of carotenoid biosynthesis with virus–derived RNA"; Proc. Natil. Acad. Sci. USA 92 (1995) 1679–1683.
Frank G. Ratcliff et al., "Gene Silencing without DNA: RNA–Mediated Cross–Protection between Viruses"; The Plant Cell, vol. 11, 1207–1215, Jul. 1999.
M. Teresa Ruiz et al., "Initiation and Maintenance of Virus–Induced Gene Silencing"; The Plant Cell, vol. 10, 937–946, Jun. 1998.

Hernandez et al., "Sequence of RNA 2 of a nematode–transmissible isolate of tobacco rattle virus"; Journal of General Virology (1995) 76, 2847–2851.
Stuart A. MacFarlane, "Molecular biology of the tobraviruses"; Journal of General Virology (1999), 80, 2799–2807.
Stuart A. MacFarlane et al., "Efficient Expression of Foreign Proteins in Roots from Tobravirus Vectors"; Virology 267, 29–35 (2000).
Herman B. Scholthof, "Rapid Delivery of Foreign Genes into Plants by Direct Rub–Inoculation with Intact Plasmid DNA of a Tomato Bushy Stunt Virus Gene Vector"; Journal of Virology, Sep. 1999, 7823–7829.
Koedtham Gopinath et al., "Engineering Cowpea Mosaic Virus RNA–2 into a Vector to Express Heterologous Proteins in Plants"; Virology 267, 159–173 (2000).

(List continued on next page.)

Primary Examiner—Robert A. Schwartzman
Assistant Examiner—Janice Li
(74) Attorney, Agent, or Firm—Dann, Dorfman, Herrell and Skillman

(57) ABSTRACT

Disclosed are nucleic acid vectors which comprise: (a) a transfer nucleotide sequence comprising (i) a plant active promoter, operably linked to (ii) a recombinant tobacco rattle virus (TRV) cDNA (preferably derived from TRV RNA2) which includes at least cis acting elements permitting replication of the cDNA; a subgenomic promoter operably linked to a sequence encoding a TRV coat protein; and a heterologous nucleotide sequence which is foreign to the virus;(b) border sequences which permit the transfer of the transfer nucleotide sequence into a plant genome. Such vectors may be used as expression vectors or for achieving viral induced gene silencing (VIGS) of a target gene, wherein the heterologous nucleotide sequence is a targeting sequence which corresponding to that gene. Example vectors include pTV00 and vectors which are derived from PTV00 and have the characteristics thereof. Also disclosed are associated processes, methods, viruses or viral particle, kits, host cells and plant tissues.

32 Claims, 5 Drawing Sheets

OTHER PUBLICATIONS

Figure 1:
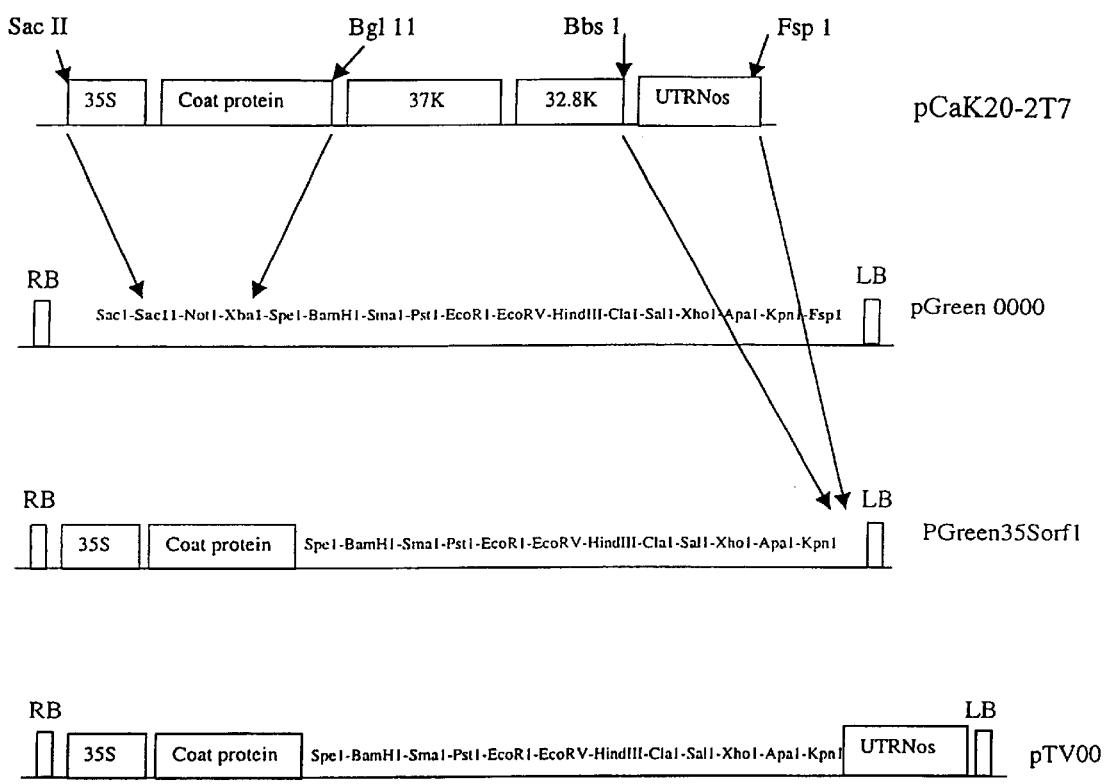

Stuart A. MacFarlane et al., "Efficient Inoculation with CaMV 35 S Promoter–Driven DNA Clones of the Tobravirus PEBV"; Virology 187, 829–831 (1992).

William D.O. Hamilton et al., Infectious RNA Produced by in vitro Transcription of a Full–length Tobacco Rattle Virus RNA–1 cDNA; J. gen. Virol. (1989), 70, 963–968.

I.R. Choi et al., "A plant virus vector for systemic expression of foreign genes in cereals"; The Plant Journal (2000) 23(4), 547–555.

Sean Chapman et al., "Potato virus X as a vector for gene expression in plants"; The Plant Journal (1992) 2(4), 549–557.

Guichang Zhang et al., "In Planta Expression of HIV–1 p24 Protein Using an RNA Plant Virus–Based Expression Vector"; Molecular Biotechnology, vol. 14, 2000, pp. 99–107.

* cited by examiner

SEQUENCE LISTING

```
<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ggcactcaac tttataaacc                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cttcagtttt ctgtcaaacc                                                     20

<210> SEQ ID NO 3
<211> LENGTH: 21
<212> TYPE: DNA
<213> ORGANISM: Artificial Sequence
```

```
<220> FEATURE:
<223> OTHER INFORMATION: Primer

<400> SEQUENCE: 3
cccctcgaga gatgtcaaat c                                          21

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
cccctcgagg cactttcatc tgg                                        23

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
cagtctagat ggcttcctca gttctttcc                                  29

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
cagggatccc acttgacgca cgttgtc                                    27

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aacatcctcg gcccacaagt t                                          21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gagctcttag agttcgtcat g                                          21

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
tggacccaga ggctttctc                                             19
```

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cttcttgtga gagagcgtca                                              20

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11 gggggatcc gggcgtaata acgcttacg                                     29

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12 gggggatcc ataaaacatt tcaatccttt g                                  31

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ttagcaccag ctatctgagc gc                                           22

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
gttccaacca gacaaacgta tgg                                          23

<210> SEQ ID NO 15
<211> LENGTH: 43
<212> TYPE: DNA
<213> ORGANISM: Artificial Sequence
<220> FEATURE:
<223> OTHER INFORMATION: Primer

<400> SEQUENCE: 15
cgtatctttg caataacagg taataatcct ctctcttgat att                    43

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
ttaaattgtc caagatcaac ctgtttaaca caagtcaacg tc            42

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
tcgcacaaaa ccaaggtgat ag            22

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
ggattattac ctgttattgc aaagatacgt ctg            33

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
tgttaaacag gttgatcttg gacaatttaa gtgc            34

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
cgtcttgctc aaggccgcga t            21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
cgacaatcta ccgattgtat g            21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
ctgcgatccc agggaaaaca g            21

<210> SEQ ID NO 23

```
<211> LENGTH: 21
<212> TYPE: DNA
<213> ORGANISM: Artificial Sequence
<220> FEATURE:
<223> OTHER INFORMATION: Primer

<400> SEQUENCE: 23
aaatgcataa agttttgcca t                                              21

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tggttgtaac catggcagag ca                                             22

<210> SEQ ID NO 25
<211> LENGTH: 13
<212> TYPE: DNA
<213> ORGANISM: Artificial Sequence
<220> FEATURE:
<223> OTHER INFORMATION: Primer

<400> SEQUENCE: 25
gaattcagat cta                                                       13

<210> SEQ ID NO 26
<211> LENGTH: 13
<212> TYPE: DNA
<213> ORGANISM: Artificial Sequence
<220> FEATURE:
<223> OTHER INFORMATION: Primer

<400> SEQUENCE: 26
acatgtagat ctg                                                       13

<210> SEQ ID NO 27
<211> LENGTH: 66
<212> TYPE: DNA
<213> ORGANISM: Artificial Sequence
<220> FEATURE:
<223> OTHER INFORMATION: Primer

<400> SEQUENCE: 27
catgaaggcc ttgacaggat atattggcgg gtaaactaag tcgctgtatg tgtttgtttg    60
agatct                                                               66

<210> SEQ ID NO 28
<211> LENGTH: 66
<212> TYPE: DNA
<213> ORGANISM: Artificial Sequence
<220> FEATURE:
<223> OTHER INFORMATION: Primer

<400> SEQUENCE: 28
catgagatct caaacaaaca catacagcga cttagtttac ccgccaatat atcctgtcaa    60
ggcctt                                                               66

<210> SEQ ID NO 29
<211> LENGTH: 73
<212> TYPE: DNA
<213> ORGANISM: Artificial Sequence
```

```
<220> FEATURE:
<223> OTHER INFORMATION: Primer

<400> SEQUENCE: 29
tccacacatt atacgagccg atgattaatt gtcaacagat cttggcagga tatattgtgg      60
tgtaaacgtt aac                                                         73

<210> SEQ ID NO 30
<211> LENGTH: 73
<212> TYPE: DNA
<213> ORGANISM: Artificial Sequence
<220> FEATURE:
<223> OTHER INFORMATION: Primer

<400> SEQUENCE: 30
ggtaacgttt acaccacaat atatcctgcc aagatctgtt gacaattaat catcggctcg      60
tataatgtgt gga                                                         73

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
cgtcaagtgc agtgcatcag t                                                21

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
gacaataggg taagttgtcc taatatgaaa                                       30

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
cattgcctcc aagcctgacg ga                                               22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
accacaggga taactggctt gt                                               22

<210> SEQ ID NO 35
<211> LENGTH: 21
<212> TYPE: DNA
<213> ORGANISM: Artificial Sequence
<220> FEATURE:
<223> OTHER INFORMATION: Primer
```

-continued

```
<400> SEQUENCE: 35
ccgacatcga aggatcaaaa a                                              21

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
cagccaagcg tcatagcgac gttg                                           24

<210> SEQ ID NO 37
<211> LENGTH: 5592
<212> TYPE: DNA
<213> ORGANISM: Artificial Sequence
<220> FEATURE:
<223> OTHER INFORMATION: pTV00

<400> SEQUENCE: 37
tttttatccc cggaagcctg tggatagagg gtagttatcc acgtgaaacc gctaatgccc      60
cgcaaagcct tgattcacgg ggctttccgg cccgctccaa aaactatcca cgtgaaatcg     120
ctaatcaggg tacgtgaaat cgctaatcgg agtacgtgaa atcgctaata aggtcacgtg     180
aaatcgctaa tcaaaaaggc acgtgagaac gctaatagcc ctttcagatc aacagcttgc     240
aaacacccct cgctccggca agtagttaca gcaagtagta tgttcaatta gcttttcaat     300
tatgaatata tatatcaatt attggtcgcc cttggcttgt ggacaatgcg ctacgcgcac     360
cggctccgcc cgtggacaac cgcaagcggt tgcccaccgt cgagcgccag cgcctttgcc     420
cacaacccgg cggccggccg caacagatcg ttttataaat ttttttttt gaaaaagaaa      480 aagcccgaaa ggcggcaacc tctcgggctt ctggatttcc gatccccgga attagatctc     540
aaacaaacac atacagcgac ttagtttacc cgccaatata tcctgtcaag gccttcatgt     600
tctttcctgc gttatcccct gattctgtgg ataaccgtat taccgccttt gagtgagctg     660
ataccgctcg ccgcagccga acgaccgagc gcagcgagtc agtgagcgag gaagcggaag     720
agcgcccaat acgcaaaccg cctctccccg cgcgttggcc gattcattaa tgcagctggc     780
acgacaggtt tcccgactgg aaagcgggca gtgagcgcaa cgcaattaat gtgagttagc     840
tcactcatta ggcaccccag gctttacact ttatgcttcc ggctcgtatg ttgtgtggaa     900
ttgtgagcgg ataacaattt cacacaggaa acagctatga ccatgattac gccaagctcg     960
gaattaaccc tcactaaagg gaacaaaagc tggagctcca ccgcggtgga gctccaccgg    1020
ggaaacctcc tcgggattcc attgcccagc tatctgtcac tttattgaga agatagtgga    1080
aaaggaaggt ggctcctaca aatgccatca ttgcgataaa ggaaaggcca tcgttgaaga    1140
tgcctctgcc gacagtggtc ccaaagatgg acccccaccc acgaggagca tcgtggaaaa    1200
agaagacgtt ccaaccacgt cttcaaagca agtggattga tgtgatatct ccactgacgt    1260
aagggatgac gcacaatccc actatccttc gcaagaccct tcctctatat aaggaagttc    1320
atttcatttg gagaggctag ataaaacatt gcacctatgg tgttgccctg ctgggggtat    1380
gtcagtgatc gcagtagaat gtactaattg acaagttgga gaatacggta gaacgtcctt    1440
atccaacaca gcctttatcc ctctcccctga cgaggttttt gtcagtgtaa tatttctttt    1500
tgaactatcc agcttagtac cgtacgggaa agtgactggt gtgcttatct ttgaaatgtt    1560
actttgggtt tcggttcttt aggttagtaa gaaagcactt gtcttctcat acaaaggaaa    1620
```

-continued

```
acctgacgta tcgcttacga aagtagcaat gaaagaaagg tggtggtttt aatcgtaccg    1680
caaaaaacga tggggtcgtt ttaattaact tctcctacaa gcgtctaaac ggacgttggg    1740
gttttgctag tttctttaga gaaaactagc taagtcttta atgttatcat tagagatggc    1800
ataaatataa tacttgtgtc tgctgataag atcattttaa tttggacgat tagacttgtt    1860
gaactacagg ttactgaatc acttgcgcta atcaacatgg gagatatgta cgatgaatca    1920
tttgacaagt cgggcggtcc tgctgacttg atggacgatt cttgggtgga atcagtttcg    1980
tggaaagatt tgttgaagaa gttacacagc ataaaatttg cactacagtc tggtagagat    2040
gagatcactg ggttactagc ggcactgaat agacagtgtc cttattcacc atatgagcag    2100
tttccagata agaaggtgta tttccttttta gactcacggg ctaacagtgc tcttggtgtg    2160
attcagaacg cttcagcgtt caagagacga gctgatgaga agaatgcagt ggcgggtgtt    2220
acaaatattc ctgcgaatcc aaacacaacg gttacgacga accaagggag tactactact    2280
accaaggcga cactggctc gactttggaa gaagacttgt acacttatta caaattcgat    2340
gatgcctcta cagcttttcca caaatctcta acttcgttag agaacatgga gttgaagagt    2400
tattaccgaa ggaactttga gaaagtattc gggattaagt ttggtggagc agctgctagt    2460
tcatctgcac cgcctccagc gagtggaggt ccgatacgtc ctaatcccta gggatttaag    2520
gacgtgaact ctgttgagat cctagaacta gtggatcccc cgggctgcag gaattcgata    2580
tcaagcttat cgataccgtc gacctcgagg ggggcccgg tacccaattc gccctatagt    2640
gagtcgtatt acaattcact ggccgtcgtt ttacaacgtc gtgactggga aaaccctggc    2700
gttacccaac ttaatcgcct tgcagcacat ccccctttcg ccagctggcg taatagcgaa    2760
gaggcccgca ccgatcgccc ttcccaacag ttgcgaagac attaaactac ggttctttaa    2820
gtagatccgt gcctgaagtt ttaggttcaa tttaaaccta cgagattgac attctcgact    2880
gatcttgatt gatcggtaag tcttttgtaa tttaattttc ttttttgattt tattttaaat    2940 tgttatctgt ttctgtgtat agactgtttg agatcggcgt ttggccgact cattgtctta    3000
ccatagggga acggactttg tttgtgttgt tattttattt gtatttatt aaaattctca    3060 acgatctgaa aaagcctcgc ggctaagaga ttgttggggg gtgagtaagt acttttaaag    3120
tgatgatggt tacaaaggca aaggggtaa aaccccctcgc ctacgtaagc gttattacgc    3180
cctcgagtat cgaattgctg caggcatgca agcgatcccc gatcgttcaa acatttggca    3240
ataaagtttc ttaagattga atcctgttgc cggtcttgcg atgattatca tataatttct    3300
gttgaattac gttaagcatg taataattaa catgtaatgc atgacgttat ttatgagatg    3360 ggttttatg attagagtcc cgcaattata catttaatac gcgatagaaa acaaaatata    3420
gcgcgcaaac taggataaat tatcgcgcgc ggtgtcatct atgttactag atcgggaatt    3480
gccaagctgc ttggcactgg ccgtcgtttt acaacgtcgt gactgggaaa accctggcgt    3540
tacccaactt aatcgccttg cagcacatcc ccctttcgcc agctggcgta atagcgaaga    3600
ggcccgcacc gatcgccctt cccaacagtt gcgcagcctg aatggcgaat ggcgcgaaat    3660
tgtaaacgtt aatgttaacg ttacaccaca atatatcctg ccaagatctc atgtgagcaa    3720
aaggccagca aaaggccagg aaccgtaaaa aggccgcgtt gctggcgttt ttccataggc    3780
tccgcccccc tgacgagcat cacaaaaatc gacgctcaag tcagaggtgg cgaaacccga    3840
caggactata aagataccag gcgtttcccc ctggaagctc cctcgtgcgc tctcctgttc    3900
cgaccctgcc gcttaccgga tacctgtccg cctttctccc ttcgggaagc gtggcgcttt    3960
```

-continued

```
ctcatagctc acgctgtagg tatctcagtt cggtgtaggt cgttcgctcc aagctgggct   4020
gtgtgcacga acccccgtt cagcccgacc gctgcgcctt atccggtaac tatcgtcttg   4080
agtccaaccc ggtaagacac gacttatcgc cactggcagc agccactggt aacaggatta   4140
gcagagcgag gtatgtaggc ggtgctacag agttcttgaa gtggtggcct aactacggct   4200
acactagaag gacagtattt ggtatctgcg ctctgctgaa gccagttacc ttcggaaaaa   4260
gagttggtag ctcttgatcc ggcaaacaaa ccaccgctgg tagcggtggt ttttttgttt   4320
gcaagcagca gattacgcgc agaaaaaaag gatctcaaga agatcctttg atcttttcta   4380
cggggtctga cgctcagtgg aacgaaaact cacgttaagg gattttggtc atggttacaa   4440
ccaattaacc aattctgatt agaaaaactc atcgagcatc aaatgaaact gcaatttatt   4500
catatcagga ttatcaatac catatttttg aaaaagccgt ttctgtaatg aaggagaaaa   4560
ctcaccgagg cagttccata ggatggcaag atcctggtat cggtctgcga ttccgactcg   4620
tccaacatca atacaaccta ttaatttccc ctcgtcaaaa ataaggttat caagtgagaa   4680
atcaccatga gtgacgactg aatccggtga gaatggcaaa agtttatgca tttctttcca   4740
gacttgttca acaggccagc cattacgctc gtcatcaaaa tcactcgcat caaccaaacc   4800
gttattcatt cgtgattgcg cctgagcgag acgaaatacg cgatcgctgt taaaaggaca   4860
attacaaaca ggaatcgaat gcaaccggcg caggaacact gccagcgcat caacaatatt   4920
ttcacctgaa tcaggatatt cttctaatac ctggaatgct gttttccctg ggatcgcagt   4980
ggtgagtaac catgcatcat caggagtacg gataaaatgc ttgatggtcg gaagaggcat   5040
aaattccgtc agccagttta gtctgaccat ctcatctgta acatcattgg caacgctacc   5100
tttgccatgt ttcagaaaca actctggcgc atcgggcttc ccatacaatc catagattgt   5160
cgcacctgat tgcccgacat tatcgcgagc ccatttatac ccatataaat cagcatccat   5220
gttggaattt aatcgcggcc tggagcaaga cgtttcccgt tgaatatggc tcataacacc   5280
ccttgtatta ctgtttatgt aagcagacag ttttattgtt catgatgata tatttttatc   5340
ttgtgcaatg taacatcaga gattttgaga cacaacgtgg ctttgttgaa taaatcgaac   5400
ttttgctgag ttgaaggatc agatcacgca tcttcccgac aacgcagacc gttccgtggc   5460
aaagcaaaag ttcaaaatca ccaactggtc cacctacaac aaagctctca tcaaccgtgc   5520
tccctcactt tctggctgga tgatggggcg attcaggcga tccccatcca acagcccgcc   5580
gtcgagcggg ct                                                         5592
```

<210> SEQ ID NO 38
<211> LENGTH: 249
<212> TYPE: DNA
<213> ORGANISM: Artificial Sequence
<220> FEATURE:
<223> OTHER INFORMATION: PEBV coat protein promoter

<400> SEQUENCE: 38

```
ggatccgcac acaaggttaa aaacgctgta gtaatacatg cgcaagaaca ggctgagcat     60
cttgttctgg ggtttcacac tatctttaga gaaagtgtta agttaattaa gttatcttaa    120
ttaagagcat aattatactg atttgtctct cgttgataga gtctatcatt ctgttctaaa    180
aatttgacaa ctcggtttgc tgacctactg gttactgtat cacttacccg agttaacgag    240
ggcgcgccc                                                            249
```

<210> SEQ ID NO 39
<211> LENGTH: 409

```
<212> TYPE: DNA
<213> ORGANISM: Artificial Sequence
<220> FEATURE:
<223> OTHER INFORMATION: N. benthamiana pds partial cDNA sequence

<400> SEQUENCE: 39
tctgtcaaac catatatgga catttatcac aggaactccc actagcttct ccaacttttg      60
gaaatatggg atctctttcc agtcttcagg caaaagaagc ttcaagatat ccactggagt     120
ggcaaacaca aaagcatctc ctttaattgt actgccatta ttctgtataa aacatttgac     180
acttccatcc tcattcagct cgatctttt tattcgtgag tttagtctga cttggccacc      240
ttttgactca atatgttcca caatcggcat gcaaagtctc tcaggagggt taccatctaa     300
aaaggccatt tttgaaccat gtttctcctg aagaaatctg ttcaaagcaa tcaagatgca     360
ctgcatcgaa agctcgtcag ggtttataaa gttgagtgcc tctagactg                 409

<210> SEQ ID NO 40
<211> LENGTH: 1773
<212> TYPE: DNA
<213> ORGANISM: Artificial Sequence
<220> FEATURE:
<223> OTHER INFORMATION: A. thaliana pds partial cDNA sequence

<400> SEQUENCE: 40
ctcgagagat gtcaaatctg tgagattcat ttactgaaga gagtaaggtt aagtttggat      60
tgcaatgaga tttatacaca ataataatg cttacaagca atcatctttt aagttttgtc     120
ctcttctcat gatgatgata ctgttgcctc cgacaacttt cttggtccag acgcagccag     180
tagctcgtaa tcctgaacaa tagactgaga gcagaatttg ccagagagga cagcgccttc     240
catggaagct aagtacttct gttttgtgta atctccagct aagtagaatc cttcaatagg     300
tgatctttgt agaggacgac atggttcaca gtttgggatg gtcttgtaca cagatcttgg     360
agtcttaacg acatggtact tcagaatttt agctttgctt tggtcagctg agatttcatc     420
agggaagagt ttctcaagtt ctttcattgt tgcatctatg atgtcagaat cagtccgtga     480
tatccattcc tctgctggtg caaatactag ctccagcatt gaccggttag gatcgtaata     540
ttccttacaa gttaaggaca tgtcggcata acgctcaga aggttacttc tgctaaagag      600
taggtgatca tatgtgttct tcagttttcg atcaaaccat atatgaacat taataactgg     660
tactccaact aatttatcca atttcttgaa gtacggtatt tctttccagg gatctggtaa     720
aaggagcttc aggatatcga ctggagcggc aaacacataa gcgtctcctt cgacagtgct     780
tccattagtg agtaagaaac tcttaaccgt gccatcgtca ttgagctcaa ttttctttat     840
cctagaatta agttgcactt ccccacctag tgatcgaata tgatccacta ctggcataca     900
aagcctttcc ggaggattac catccaagaa tgccatcttg aaccatgtt tttcctgaag     960 aaaccggttc aaagctatca aaatgcattg cattgacagt tcatcagggt ttataaagtt    1020
tagcgccttt gacatggcaa taaacacctc gtcggtcacg cgctcaggta ctccctgctt    1080
ttccatccat tctttgactg ataaaccatc ttgggcctca ataagcct gaccgccgac      1140 catggctggc aaaagtccaa tagcaaactt tatttctct ggccatgtca gcatctcgtt     1200
gttccgcaaa atagcccaaa taccatttaa gggtgctggt aggacatctg ggaagtcaaa    1260
tctactaaat tctccaggtt tacttggcat agcaaaaatc atggagtgtt ccttccactg    1320
caaccgatca ttgatcccaa gttctccaaa taaattctgc acattcggat aagcaccgaa    1380
gaaaatatgt aaaccagtct cataccagtc cccatcttca tccttccatg cagctatctt    1440
```

```
tccaccaaga acatctcttg cttcaagcaa cagaggtttg tggcctgcat cagccaggta    1500
ctttgcagtt gacaatccag ccaatccagc accagcaatt acaactttca aaggcttagc    1560
aggacgagga gcactacgga aggatgcaga taaactagca gcttccaaga aattgacagt    1620
gttctctagc tctggccttg aatatccac acaaactacc tgcaaaggac cagcagtact     1680
cctcctcctt gttcttgtct taagcgcttg agaagtggga accctaaagc tatgtcccat    1740
tagttcacaa cctccagatg aaagtgcctc gag                                 1773

<210> SEQ ID NO 41
<211> LENGTH: 499
<212> TYPE: DNA
<213> ORGANISM: Artificial Sequence
<220> FEATURE:
<223> OTHER INFORMATION: N. benthamiana rubisco partial cDNA sequence

<400> SEQUENCE: 41
agtctagatg gcttcctcag ttctttcctc tgcagcagtt gccacccgca gcaatgttgc      60
tcaagctaac atggttgcac ctttcactgg ccttaagtca gctgcctcat tccctgtttc     120
aaggaagcaa aaccttgaca tcacttccat tgccagcaac ggcggaagag tgcaatgcat    180
gcaggtgtgg ccaccaatta acaagaagaa gtacgagact ctctcatacc ttcctgattt    240
gagccaggag caattgctta gtgaagttga gtaccttttg aaaaatggat gggttccttg    300
cttggaattc gagactgagc acggatttgt ctaccgtgaa acaacaagt caccaggata     360 ctatgatggc agatactgga ccatgtggaa gctaccatt tcggatgcac tgatgccacc     420
caagtgttgg ctgaggtgga agaggcgaag aaggcatacc cacaggcctg gatccgtatc    480
attggattcg acaacgtgg                                                 499

<210> SEQ ID NO 42
<211> LENGTH: 321
<212> TYPE: DNA
<213> ORGANISM: Artificial Sequence
<220> FEATURE:
<223> OTHER INFORMATION: Partial cDNA sequence from the 3' end of GFP

<400> SEQUENCE: 42
gatggaaaca ttcttggaca caaattggaa tacaactata actcacacaa tgtatacatc      60
atggcagaca acaaaagaa tggaatcaaa gttaacttca aaattagaca caacattgaa     120
gatggaagcg ttcaactagc agaccattat caacaaaata ctccaattgg cgatggccct    180
gtccttttac cagacaacca ttacctgtcc acacaatctg cccttcgaa agatcccaac     240 gaaaagagag accacatggt ccttcttgag tttgtaacag ctgctgggat tacacatggc    300
atggatgaac tatacaaata a                                              321

<210> SEQ ID NO 43
<211> LENGTH: 421
<212> TYPE: DNA
<213> ORGANISM: Artificial Sequence
<220> FEATURE:
<223> OTHER INFORMATION: N. benthamiana partial cDNA sequence from NFL

<400> SEQUENCE: 43
tggacccaga ggctttctca gcgagtttgt tcaaatggga ccctagaggt gcaatgccac       60
cgccaacccg gctgtggaa gccgcggtgg cgcctcctcc tccaccacca gttctgccac      120
cgccgcagcc tctatcggcg gcctattcca ttaggacaag ggagttagga gggctagagg    180
agttgtttca agcttacggt atacgttatt acactgctgc taaaatagcg gagctaggtt    240
```

```
ttacggtgaa tactctattg gacatgaaag atgaggaact tgatgatatg atgaatagcc       300
tttcacagat tttcagatgg gaactcctcg tcggagaaag gtacggtatc aaagctgcaa       360
tcagggcgga acggcggagg cttgaggagg aagaactacg gcggcgcagc caccttctgt       420
c                                                                      421

<210> SEQ ID NO 44
<211> LENGTH: 8976
<212> TYPE: DNA
<213> ORGANISM: Artificial Sequence
<220> FEATURE:
<223> OTHER INFORMATION: Complete sequence of pBINTRA6 plasmid

<400> SEQUENCE: 44
tactccaaaa atgtcaaaga tacagtctca gaagaccaaa gggctattga acttttcaa         60 caaagggtaa tttcgggaaa cctcctcgga ttccattgcc cagctatctg tcacttcatc       120
gaaaggacag tagaaaagga aggtggctcc tacaaatgcc atcattgcga taaaggaaag       180
gctatcattc aagatgcctc tgccgacagt ggtcccaaag atggaccccc acccacgagg       240
agcatcgtgg aaaaagaaga cgtcccaacc acgtcttcaa agcaagtgga ttgatgtgac       300
atctccactg acgtaaggga tgacgcacaa tcccactatc cttcgcaaga cccttcttct       360
atataaggaa gttcatttca tttggagagg acagcccaag cttctagag gatccataaa       420 acatttcaat cctttgaacg cggtagaacg tgctaattgg attttggtga aacgcggta       480 gaacgtactt atcacctaca gttttatttt gtttttcttt ttggtttaat ctatccagct     540
tagtaccgag tggggaaaag tgactggtgt gcctaaaacc ttttctttga tactttgtaa       600
aaatacatac agatacaatg gcgaacggta acttcaagtt gtctcaattg ctcaatgtgg       660
acgagatgtc tgctgagcag aggagtcatt tctttgactt gatgctgact aaacctgatt       720
gtgagatcgg gcaaatgatg caaagagttg ttgttgataa agtcgatgac atgattagag       780
aaagaaagac taaagatcca gtgattgttc atgaagttct ttctcagaag gaacagaaca       840
agttgatgga aatttatcct gaattcaata tcgtgtttaa agacgacaaa aacatggttc       900 atgggttgc ggctgctgag cgaaaactac aagctttatt gcttttagat agagttcctg       960
ctctgcaaga ggtggatgac atcggtggtc aatggtcgtt tgggtaact agaggtgaga      1020 aaaggattca ttcctgttgt ccaaatctag atattcggga tgatcagaga gaaatttctc      1080
gacagatatt tcttactgct attggtgatc aagctagaag tggtaagaga cagatgtcgg      1140
agaatgagct gtggatgtat gaccaatttc gtgaaaatat tgctgcgcct aacgcggtta      1200
ggtgcaataa tacatatcag ggttgtacat gtaggggttt tctgatggt aagaagaaag       1260 gcgcgcagta tgcgatagct cttcacagcc tgtatgactt caagttgaaa gacttgatgg      1320
ctactatggt tgagaagaaa actaaagtgg ttcatgctgc tatgcttttt gctcctgaaa      1380
gtatgttagt ggacgaaggt ccattacctt ctgttgacgg ttactacatg aagaagaacg      1440
ggaagatcta tttcggtttt gagaaagatc cttcctttc ttacattcat gactgggaag       1500
agtacaagaa gtatctactg gggaagccag tgagttacca agggaatgtg ttctacttcg      1560
aaccgtggca ggtgagagga gacacaatgc ttttttcgat ctacaggata gctggagttc      1620
cgaggaggtc tctatcatcg caagagtact accgaagaat atatatcagt agatgggaaa      1680
gcatggttgt tgtcccaatt ttcgatctgg tcgaatcaac gcgagagttg gtcaagaaag      1740 acctgttttgt agagaaacaa ttcatggaca agtgtttgga ttacatagct aggttatctg      1800
```

-continued

```
accagcagct gaccataagc aatgttaaat catacttgag ttcaaataat tgggtcttat      1860
tcataaacgg ggcggccgtg aagaacaagc aaagtgtaga ttctcgagat ttacagttgt      1920
tggctcaaac tttgctagtg aaggaacaag tggcgagacc tgtcatgagg gagttgcgtg      1980
aagcaattct gactgagacg aaacctatca cgtcattgac tgatgtgctg ggtttaatat      2040
caagaaaact gtggaagcag tttgctaaca agatcgcagt cggcggattc gttggcatgg      2100
ttggtactct aattggattc tatccaaaga aggtactaac ctgggcgaag gacacaccaa      2160
atggtccaga actatgttac gagaactcgc acaaaaccaa ggtgatagta tttctgagtg      2220
ttgtgtatgc cattggagga atcacgctta tgcgtcgaga catccgagat ggactggtga      2280
aaaaactatg tgatatgttt gatatcaaac gggggccca tgtcttagac gttgagaatc      2340
cgtgccgcta ttatgaaatc aacgatttct ttagcagtct gtattcggca tctgagtccg      2400
gtgagaccgt tttaccagat ttatccgagg taaaagccaa gtctgataag ctattgcagc      2460
agaagaaaga aatcgctgac gagtttctaa gtgcaaaatt ctctaactat tctggcagtt      2520
cggtgagaac ttctccacca tcggtggtcg gttcatctcg aagcggactg ggtctgttgt      2580
tggaagacag taacgtgctg acccaagcta gagttggagt ttcaagaaag gtagacgatg      2640
aggagatcat ggagcagttt ctgagtggtc ttattgacac tgaagcagaa attgacgagg      2700
ttgtttcagc cttttcagct gaatgtgaaa gaggggaaac aagcggtaca aagtgttgt       2760
gtaaacctt aacgccacca ggatttgaga acgtgttgcc agctgtcaaa cctttggtca      2820
gcaaaggaaa aacggtcaaa cgtgtcgatt acttccaagt gatgggaggt gagagattac      2880
caaaaaggcc ggttgtcagt ggagacgatt ctgtggacgc tagaagagag tttctgtact      2940
acttagatgc ggagagagtc gctcaaaatg atgaaattat gtctctgtat cgtgactatt      3000
cgagaggagt tattcgaact ggaggtcaga attacccgca cggactggga gtgtgggatg      3060
tggagatgaa gaactggtgc atacgtccag tggtcactga acatgctat gtgttccaac       3120
cagacaaacg tatggatgat tggtcgggat acttagaagt ggctgtttgg gaacgaggta      3180
tgttggtcaa cgacttcgcg gtcgaaagga tgagtgatta tgtcatagtt tgcgatcaga      3240
cgtatctttg caataacagg taataatcct ctctcttgat atttttaaat tatagaatta      3300
attagtttac tttattcttt actatatgat ttaaatagtt taatcttgtt tttgagtaaa      3360
ctattcgatt ttgatatttg tattcgtcct acaaagttgg aaatactgat gatattttct      3420
tttgaacgtg atacctacca atactaatct tacggaatct tttaatagag cactaatcaa      3480
catggaacta agaccaatt cttaagtgtc tctgttgtac agttcatttt agtagtgcgt       3540
ttaagtatta ttatctccct tcatgcgggg caattatgta gattaaaatc gaattatat       3600
aaaatttaca taagtctaag tctagggtct ccagctaatt gttatttttt taacgatgtt      3660
gactaaagca ataacgacgt tgacttgtgt taaacaggtt gatcttggac aatttaagtg      3720
ccctggatct aggaccagtt aactgttctt ttgaattagt tgacggtgta cctggttgtg      3780
gtaagtcgac aatgattgtc aactcagcta atccttgtgt cgatgtggtt ctctctactg      3840
ggagagcagc aaccgacgac ttgatcgaga gattcgcgag caaaggtttt ccatgcaaat      3900
tgaaaaggag agtgaagacg gttgattctt ttttgatgca ttgtgtcgat ggttctttaa      3960
ccggagacgt gttgcatttc gacgaagctc tcatggccca tgctggtatg gtgtactttt      4020
gcgctcagat agctggtgct aaacgatgta tctgtcaagg agatcagaat caaatttctt      4080
tcaagcctag ggtatctcaa gttgatttga ggttttctag tctggtcgga aagtttgaca      4140
ttgttacaga aaaaagagaa acttacagaa gtccagcaga tgtggctgcc gtattgaaca      4200
```

-continued

```
agtactatac tggagatgtc agaacacata acgcgactgc taattcgatg acgtgagga    4260 agattgtgtc taaagaacag gtttctttga agcctggtgc tcagtacata actttccttc    4320
agtctgagaa gaaggagttg gtaaatttgt tggcattgag gaaagtggca gctaaagtga    4380
gtacagtaca cgagtcgcaa ggagagacat tcaaagatgt agtcctagtc aggacgaaac    4440
ctacggatga ctcaatcgct agaggtcggg agtacttaat cgtggcattg tcgcgtcaca    4500
cacaatcact tgtgtatgaa actgtgaaag aggacgatga agcaaagag atcagggaaa     4560 gtgccgcgct tacgaaggcg gctttggcaa gattttttgt tactgagacc gtcttatgac    4620
ggtttcggtc taggtttgat gtctttagac atcatgaagg gccttgcgcc gttccagatt    4680
caggtacgat tacggacttg gagatgtggt acgacgcttt gtttccggga aattcgttaa    4740
gagactcaag cctagacggg tatttggtgg caacgactga ttgcaatttg cgattagaca    4800
atgttacgat caaaagtgga aactggaaag acaagtttgc tgaaaagaa acgtttctga     4860 aaccggttat tcgtactgct atgcctgaca aaggaagac tactcagttg gagagtttgt      4920
tagcattgca gaaaaggaac caagcggcac ccgatctaca agaaaatgtg cacgcgacag    4980
ttctaatcga agagacgatg aagaagctga atctgttgt ctacgatgtg ggaaaaattc     5040
gggctgatcc tattgtcaat agagctcaaa tggagagatg gtggagaaat caaagcacag    5100
cggtacaggc taaggtagta gcagatgtga gagagttaca tgaaatagac tattcgtctt    5160
acatgtatat gatcaaatct gacgtgaaac ctaagactga tttaacaccg caatttgaat    5220
actcagctct acagactgtt gtgtatcacg agaagttgat caactcgttg ttcggtccaa    5280
ttttcaaaga aattaatgaa cgcaagttgg atgctatgca accacatttt gtgttcaaca    5340
cgagaatgac atcgagtgat ttaaacgatc gagtgaagtt cttaaatacg gaagcggctt    5400
acgactttgt tgagatagac atgtctaaat tcgacaagtc ggcaaatcgc ttccatttac    5460
aactgcagct ggagatttac aggttatttg ggctggatga gtgggcggcc ttcctttggg    5520
aggtgtcgca cactcaaact actgtgagag atattcaaaa tggtatgatg gcgcatattt    5580
ggtaccaaca aaagagtgga gatgctgata cttataatgc aaaattcagat agaacactgt   5640 gtgcactctt gtctgaatta ccattggaga aagcagtcat ggttacatat ggaggagatg    5700
actcactgat tgcgtttcct agaggaacgc agtttgttga tccgtgtcca aagttggcta    5760
ctaagtggaa tttcgagtgc aagatttta agtacgatgt cccaatgttt tgtgggaagt     5820
tcttgcttaa gacgtcatcg tgttacgagt tcgtgccaga tccggtaaaa gttctgacga    5880
agttggggaa aaagagtata aaggatgtgc aacatttagc cgagatctac atctcgctga    5940
atgattccaa tagagctctt gggaactaca tggtggtatc caaactgtcc gagtctgttt    6000
cagaccggta tttgtacaaa ggtgattctg ttcatgcgct ttgtgcgcta tggaagcata    6060
ttaagagttt tacagctctg tgtacattat tccgagacga aaacgataag gaattgaacc    6120
cggctaaggt tgattggaag aaggcacaga gagctgtgtc aaacttttac gactggtaat    6180
atggaagaca agtcattggt caccttgaag aagaagactt tcgaagtctc aaaattctca    6240
aatctagggg ccattgaatt gtttgtggac ggtaggagga agagaccgaa gtattttcac    6300
agaagaagag aaactgtcct aaatcatgtt ggtgggaaga agagtgaaca caagttagac    6360 gttttttgacc aaagggatta caaaatgatt aaatcttacg cgtttctaaa ggtagtaggt    6420
gtacaactag ttgtaacatc acatctacct gcagatacgc ctgggttcat tcaaatcgat    6480
ctgttggatt cgagacttac tgagaaaaga aagagaggaa agactattca gagattcaaa    6540
```

-continued

```
gctcgagctt gcgataactg ttcagttgcg cagtacaagg ttgaatacag tatttccaca    6600
caggagaacg tacttgatgt ctggaaggtg ggttgtattt ctgaggcgt tccggtctgt     6660
gacggtacat accctttcag tatcgaagtg tcgctaatat gggttgctac tgattcgact    6720
aggcgcctca atgtggaaga actgaacagt tcggattaca ttgaaggcga ttttaccgat    6780
caagaggttt tcggtgagtt catgtctttg aaacaagtgg agatgaagac gattgaggcg    6840
aagtacgatg gtccttacag accagctact actagaccta agtcattatt gtcaagtgaa    6900
gatgttaaga gagcgtctaa taagaaaaac tcgtcttaat gcataaagaa atttattgtc    6960
aatatgacgt gtgtactcaa gggttgtgtg aatgaagtca ctgttcttgg tcacgagacg    7020
tgtagtatcg gtcatgctaa caaattgcga agcaagttg ctgacatggt tggtgtcaca     7080
cgtaggtgtg cggaaaataa ttgtggatgg tttgtctgtg ttgttatcaa tgattttact    7140
tttgatgtgt ataattgttg tggccgtagt caccttgaaa agtgtcgtaa acgtgttgaa    7200
acaagaaatc gagaaatttg gaaacaaatt cgacgaaatc aagctgaaaa catgtctgcg    7260
acagctaaaa agtctcataa ttcgaagacc tctaagaaga aattcaaaga ggacagagaa    7320
tttgggacac caaaaagatt tttaagagat gatgttcctt tcgggattga tcgtttgttt    7380
gcttttgat tttattttat attgttatct gtttctgtgt atagactgtt tgagattggc     7440
gcttggccga ctcattgtct taccatagg gaacggactt tgtttgtgtt gttattttat     7500
ttgtattta ttaaaattct caatgatctg aaaaggcctc gaggctaaga gattattggg     7560
gggtgagtaa gtacttttaa agtgatgatg gttacaaagg caaagggt aaacccctc       7620
gcctacgtaa gcgttattac gcccggatcc ccgggggagc tcgaattcgc tgaaatcacc    7680
agtctctctc tacaaatcta tctctctcta ttttttccat aaataatgtg tgagtagttt    7740
cccgataagg gaaattaggg ttcttatagg gtttcgctca tgtgttgagc atataagaaa    7800
cccttagtat gtatttgtat ttgtaaaata cttctattat caataaaatt tctaattcct    7860
aaaaccaaaa tccagtacta aaatccagat ctcctaaagt ccctatagat ctttgtcgtg    7920
aatataaacc agacacgaga cgactaaacc tggagcccag acgccgttcg aagctagaag    7980
taccgcttag gcaggaggcc gttagggaaa agatgctaag gcagggttgg ttacgttgac    8040
tcccccgtag gtttggttta aatatgatga agtggacgga aggaaggagg aagacaagga    8100
aggataaggt tgcaggccct gtgcaaggta agaagatgga aatttgatag aggtacgcta    8160
ctatacttat actatacgct aagggaatgc ttgtatttat acctatacc ccctaataac     8220
cccttatcaa tttaagaaat aatccgcata agcccccgct taaaaattgg tatcagagcc    8280
atgaataggt ctatgaccaa aactcaagag gataaaacct caccaaaata cgaaagagtt    8340
cttaactcta aagataaaag atctttcaag atcaaaacta gttccctcac accggagcat    8400
gcgatatcct cgacctgcag gcatgcaagc ttggcgtaat catggtcata gctgtttcct    8460
gtgtgaaatt gttatccgct cacaattcca cacaacatac gagccggaag cataaagtgt    8520
aaagcctggg gtgcctaatg agtgagctaa ctcacattaa ttgcgttgcg ctcactgccc    8580
gctttccagt cgggaaacct gtcgtgccag ctgcattaat gaatcggcca acgcgcgggg    8640
agaggcggtt tgcgtattgg gccaaagaca aagggcgac attcaaccga ttgagggagg     8700
gaaggtaaat attgacggaa attattcatt aaaggtgaat tatcaccgtc accgacttga    8760
gccatttggg aattagagcc agcaaaatca ccagtagcac cattaccatt agcaaggccg    8820
gaaacgtcac caatgaaacc atcgatagca gcaccgtaat cagtagcgac agaatcaagt    8880
ttgcctttag cgtcagactg tagcgcgttt tcatcggcat tttcggtcat agccccctta    8940
```

```
ttagcgtttg ccatcttttc ataatcaaaa tcaccg                                      8976

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
ggatccgcac acaaggtta                                                           19

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
gggcgcgccc tcgttaac                                                            18
```

RECOMBINANT PLANT VIRAL VECTORS

TECHNICAL FIELD

The present invention relates generally to recombinant plant viral nucleic acids, and methods of use thereof.

PRIOR ART

Recombinant plant viral nucleic acids are of interest generally for their utility as expression vectors in plants.

Additionally, such nucleic acids can be used to initiate virus induced gene silencing (VIGS). This phenomenon is based on the observation that virus infection in plants can initiate sequence-specific nucleic-acid based defence mechanisms that resemble either transcriptional, or post-transcriptional gene silencing (PTGS) (Covey, Al-Kaff 1997; Ratcliff, Harrison et al. 1997; Al-Kaff, Covey et al. 1998). PTGS is also manifest as an inhibition of nuclear gene expression when a virus is modified to carry sequence from a nuclear expressed gene (Kumagai, Donson et al. 1995; Kjemtrup, Sampson et al. 1998; Ruiz, Voinnet et al. 1998). PTGS can also cause recovery from viral infection when a plant expressing a transgene derived from viral cDNA is infected by a homologous virus (Lindbo, Silva-Rosales et al. 1993; Guo and Garcia 1997). Both the inhibition of nuclear gene expression, and recovery from viral infection are caused by sequence-specific RNA degradation.

Because modified viruses inhibit the expression of homologous plant genes, VIGS can be used to induce an apparent null-phenotype or a loss of function and therefore identify the function of any gene. Viruses that have been modified in this manner include tobacco mosaic virus (TMV) (Kumagai, Donson et al. 1995) potato virus X (PVX) (Ruiz, Voinnet et al. 1998), and tomato golden mosaic virus (Kjemtrup, Sampson et al. 1998).

DISCLOSURE OF THE INVENTION

The present invention is concerned with novel recombinant plant viral nucleic acids.

In preferred forms the present invention is concerned with providing VIGS-based methods and materials which may be more suitable as a tool for functional genomics than those which have been used in the past. For instance TMV, PVX and TGMV infections cause significant symptoms, such as a chlorosis, leaf-distortion and necrosis. Phenotypes caused by VIGS of a plant gene can therefore be hard to differentiate from these viral symptoms. Secondly, like most viruses, TMV, PVX and TGMV form mosaic, vein-based infections, and therefore do not cause confluent VIGS across the whole leaf. Leaves may therefore contain a mixture of cells with and without VIGS, complicating interpretation of any phenotype. Thirdly, TMV, PVX and TGMV do not infect meristems (Matthews 1991) and can not therefore inhibit expression of genes that determine the identity and development of plant tissue. Finally, although the first plant genome to be fully sequenced will be that of *Arabidopsis thaliana*, TMV, PVX and TGMV vectors do not infect this plant. Therefore the potential of VIGS to identify gene function in Arabidopsis is limited with available technology. A VIGS vector which overcame one or more of these drawbacks would therefore represent a contribution to the art.

The present inventors have developed novel recombinant cDNA viral constructs based on tobacco rattle virus (TRV) which in preferred forms are particularly adapted for use with VIGS. Such vectors may induce few or no symptoms, cause confluent VIGS across the leaf, operate in Nicotiana species and in Arabidopsis, and inhibit gene expression in meristems.

A viral expression vector based on TRV has previously been described in which non-viral proteins were expressed from a sub-genomic promoter (Ratcliff, MacFarlane et al. 1999). The viral RNA was synthesised in vitro and then inoculated into the plant. The TRV vectors of the present invention include inter alia modifications to facilitate both the insertion of plant gene sequences and the it subsequent infection of plants. Other TRV based vectors are disclosed by Hamilton & Baulcombe (1989) J. Gen. Virol 70: 963–968 and Mueller et al (1997) J. Gen. Virol 78: 2085–2088.

Thus in a first aspect of the present invention there is disclosed a nucleic acid vector which comprises:

(a) a transfer nucleotide sequence comprising (i) a plant active promoter, operably linked to (ii) a recombinant tobacco rattle virus (TRV) cDNA which includes at least cis acting elements permitting replication of said cDNA; a subgenomic promoter operably linked to a sequence encoding a TRV coat protein; and a heterologous nucleotide sequence which is foreign to said virus;

(b) border sequences which permit the transfer of the transfer nucleotide sequence into a plant cell nucleus.

The transfer nucleotide sequence is situated between the border sequences and is capable of being inserted into a plant genome under appropriate conditions. Generally this may be achieved by use of so called "agro-infiltration" which uses Agrobacterium-mediated transient transformation. Briefly, this technique is based on the property of *Agrobacterium tumafaciens* to transfer a portion of its DNA ("T-DNA") into a host cell where it may become integrated into nuclear DNA. The T-DNA is defined by left and right border sequences which are around 25 nucleotides in length. In the present invention the border sequences are included around the transfer nucleotide sequence (the T-DNA) with the whole vector being introduced into the plant by agro-infiltration, optionally in the form of a binary-transformation vector.

By "plant active promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. Nucleic acid operably linked to a promoter is "under transcriptional initiation regulation" of the promoter.

The cDNA includes cis acting elements permitting replication of said cDNA. However the vector need not include all of the sequence required to replicate and move within the plant. The vectors of the present invention will generally require supplementary proteins and/or nucleic acids from TRV in order to achieve this. Thus the cDNA may correspond to part of TRV RNA 2, and will thus require proteins encoded by TRV RNA1 for replication.

The TRV coat protein (as with other defined or recited sequences herein) need not be 'wild-type', but may optionally be a variant (e.g. mutant, or other variant, or a substantially homologous derivative) provided that its function (to encapsulate and permit movement of the TRV genome) is not negated. By "Substantially homologous" is meant that the sequence in question shares at least about 70%, or 80% identity, most preferably at least about 90%, 95%, 96%, 97%, 98% or 99% identity with the reference sequence. Identity may be at the nucleotide sequence and/or encoded amino acid sequence level. Homology may be over the full-length of the relevant sequence shown herein (e.g. in the sequence Annex) or may be over a part of it. Identity may be determined by the TBLASTN program, of Altschul et al. (1990) *J. Mol. Biol.* 215: 403–10, or BestFit, which is part of the Wisconsin Package, Version 8, September 1994, (Genetics Computer Group, 575 Science Drive, Madison, Wis., USA, Wisconsin 53711). Preferably sequence comparisons are made using FASTA and FASTP (see Pearson & Lipman, 1988. Methods in Enzymology 183: 63–98). Parameters are preferably set, using the default matrix, as follows: Gapopen (penalty for the first residue in a gap): −12 for proteins/−16 for DNA; Gapext (penalty for additional residues in a gap): −2 for proteins/−4 for DNA; KTUP word length: 2 for proteins/6 for DNA.

The heterologous nucleotide sequence is foreign (non-native) to TRV, which is to say that it does not occur naturally in the TRV viral genome at the position in which it is present in the VIGS vector. The sequence will generally be either a cloning site (to permit the insertion of a desired sequence) or a desired sequence itself.

Some preferred embodiments of the invention will now be discussed.

Vector

This is preferably based on plant binary transformation vector pGreen (see Materials and Methods below). The vector may be an expression vector (for transcription of a desired sequence, which may then be translated). Alternatively (and preferably) the vector is a "VIGS vector", by which is meant one which is adapted to cause or permit virus induced gene silencing of a desired target nucleotide sequence corresponding to a sequence included in the vector.

Nucleic acid vectors according to the present invention may be provided isolated and/or purified, in substantially pure or homogeneous form, or free or substantially free of other nucleic acid. The term "isolated" encompasses all these possibilities.

Generally speaking, in the light of the present disclosure, those skilled in the art will be able to construct vectors according to the present invention. Such vectors may include, in addition to the promoter, a suitable terminator or other regulatory sequence such as to define an expression cassette consisting of the recombinant TRV cDNA and the heterologous nucleotide sequence. For further details see, for example, *Molecular Cloning: a Laboratory Manual*: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds., John Wiley & Sons, 1992. Specific procedures and vectors previously used with wide success upon plants are described by Bevan, Nucl. Acids Res. (1984) 12, 8711–8721), and Guerineau and Mullineaux, (1993) Plant transformation and expression vectors. In: Plant Molecular Biology Labfax (Croy RRD ed) Oxford, BIOS Scientific Publishers, pp 121–148.

Plant Promoter

Suitable promoters will be well known to those skilled in the art and include the Cauliflower Mosaic Virus 35S (CaMV 35S) gene promoter that is expressed at a high level in virtually all plant tissues. The promoter may in principle be an inducible promoter such as the maize glutathione-S-transferase isoform II (GST-II-27) gene promoter which is activated in response to application of exogenous safener (WO93/01294, ICI Ltd). The GST-II-27 gene promoter has been shown to be induced by certain chemical compounds which can be applied to growing plants. Another suitable promoter may be the DEX promoter (Plant Journal (1997) 11: 605–612).

Recombinant TRV cDNA

This is preferably based on a modified, reduced, cDNA clone of TRV RNA2. In the Examples herein the strain used is ppk20. However any appropriate strain, which can give rise to replicating, infectious viral transcripts, could be used (see e.g. Macfarlane, 1999 for further examples).

Within the cDNA it is preferable that non-essential ORFs or other sequences are deleted, provided that the cDNA can still be used to generate replicating, infectious transcripts. Preferably, where the cDNA is based on TRV RNA2 of ppk20, two open reading frames (37K and 32.8K) are deleted to leave only the 5' and 3' untranslated regions and the viral gene encoding the coat-protein. The deleted ORFs are replaced by a heterologous nucleotide sequence between the coat protein and the untranslated region (UTR). The sequence is shown in the Sequence appendix (No. 1). Naturally substantially homologous variants of the sequence are also included within the scope of the invention. In particular, vectors derived from pTV00 and having the characteristics (described herein) of that vector, are also embraced.

Vectors based on TRV RNA2 require proteins encoded by TRV RNA1 for replication, which can be achieved as described below.

Heterologous Nucleotide Sequence.

This can in principle be a single or multiple cloning site (i.e. a sequence encoding two or more restriction endonuclease target sites) to facilitate the incorporation of a desired nucleotide sequence.

For expression vectors according to the present invention, the sequence will generally include or be operably linked to a subgenomic promoter which is recognised by a TRV-effective replicase (e.g. the PEBV CP subgenomic promoter) and an ORF sequence which it is desired to express and which is therefore transcribed as a subgenomic RNA.

For VIGS vectors the sequence will be a "targeting sequence" which corresponds to a sequence in a target gene, either in the sense or anti-sense orientation, or a sequence which has sufficient homology to a target sequence for down-regulation of expression of the target gene to occur. Such a targetting sequence may be included in the vector anywhere in the viral cDNA irrespective of the location of any subgenomic promoter (provided it does not interfere with the cis-acting replication elements or the coat protein). Generally speaking it will be preferable for VIGS vectors according to the present invention not to include a subgenomic promoter within or operably linked to the heterologous gene sequence. Such preferred vectors have the advantage that they are more stable (reduced likelihood of self-recombination) that those of the prior art such as those described by Ratcliff, MacFarlane et al. (1999) supra which had more than one subgenomic promoter.

In general the targeting sequence may be derived from a plant nuclear gene or transgene, or a gene on an extrachromosomal element such as a plastid.

VIGS is particularly preferred for investigating gene function in that it can be used to impose an intermediate or a null phenotype for a particular gene, which can provide information about the function of that gene in vivo. In such cases the targeting sequence may not be known, but the methods of the present invention may be used to identify it with a particular phenotype.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the relationship between target and targeting sequence. It may be preferable that there is complete sequence identity between the targeting sequence in the vector and the target sequence in the plant, although total complementarity or similarity of sequence is not essential. One or more nucleotides may differ in the targeting sequence from the target gene. Thus, a targeting sequence employed in a construct in accordance with the present invention may be a wild-type sequence (e.g. gene) selected from those available, or a substantially homologous mutant, derivative, variant or allele, by way of insertion, addition, deletion or substitution of one or more nucleotides, of such a sequence. Such a sequence need not include an open reading frame or specify an RNA that would be translatable.

A further possibility is to target a conserved sequence of a gene, e.g. a sequence that is characteristic of one or more genes in one or more pathogens against which resistance is desired, such as a regulatory sequence.

Other aspects of the invention will now be discussed.

One aspect of the present invention is a process for producing a vector as described above, the process being substantially as set out in the Examples hereinafter. A further aspect is a process for producing a vector as described above, which process comprises the step of cloning a heterologous nucleotide sequence which is a targeting sequence into the vector.

Thus one aspect of the present invention includes a method of silencing a target gene in a plant tissue using VIGS which method comprises the steps of introducing a vector as described above into the plant, wherein said vector includes a heterologous nucleotide sequence which is a targeting sequence.

"Plant tissue" is any tissue of a plant in planta or in culture, including the whole plant an organ thereof, a cutting, or any group of plant cells organised into a structural and functional unit.

"Silencing" is a term generally used to refer to suppression of expression of a gene. The degree of reduction may be so as to totally abolish production of the encoded gene product, but more usually the abolition of expression is partial, with some degree of expression remaining. The term should not therefore be taken to require complete "silencing" of expression. It is used herein where convenient because those skilled in the art well understand this.

The method may be preferably used to cause confluent VIGS of the target gene across a whole leaf and/or to silence a target gene in meristematic tissue.

As discussed above, for introduction into the plant, the vector may be in the form of an Agrobacterium binary vector. The vector is introduced into the plant cell by Agrobacterium-mediated T-DNA transfer, the transfer sequence may be integrated transiently into the plant (cell) genome, and is then transcribed to RNA from the plant promoter. In the published vector of Ratcliff, MacFarlane et al. (1999), the viral cDNA and any cDNA inserted after the sub-genomic promoter was transcribed to infectious RNA in vitro by T7 RNA polymerase and subsequently introduced into the plant.

TRV RNA 2 and all derived constructs require proteins encoded by TRV RNA1 for replication within and movement though out the plant. TRV RNA1 infections can be initiated either by rub-inoculating the plant with purified RNA 1 (Matthews 1991), or by transient Agrobacterium mediated expression in the plant of the plasmid pBINTRA6, which contains a CaMV 35S driven infectious clone of TRV PPK20 RNA 1 (see Materials and Methods).

The present invention may particularly be applied in plants which are natural hosts (compatible with) TRV. By "compatible" is meant capable of operating with the other components of a system, in this case TRV must be capable of replicating in the plant in question. These include *Arabidopsis thaliana*. Others include (but are not limited to) *Allium cepa; Amaranthus caudatus; Amaranthus retroflexus; Antirrhinum majus; snap-dragon; Arachis hypogaea; Avena sativa*; Bellis perennis; Beta vulgaris; Brassica campestris; Brassica *campestris* ssp. *napus; Brassica campestris* ssp. *pekinensis*; Brassica juncea; Calendula officinalis; Capsella bursa-pastoris; Capsicum annuum; Catharanthus roseus; Cheiranthus cheiri; Chenopodium album; Chenopodium amaranticolor; Chenopodium foetidum; Chenopodium quinoa; Coriandrum sativum; Cucumis melo; Cucumis sativus; Glycine max; Gomphrena globosa; Gypsophila elegans; Helianthus annuus; Hyacinthus; Hyoscyamus niger; Lactuca sativa; Lathyrus odoratus; Linum usitatissimum; Lobelia erinus; Lupinus mutabilis; Lycopersicon esculentum; Lycopersicon pimpinellifolium; Melilotus albus; Momordica balsamina; Myosotis sylvatica; Narcissus pseudonarcissus; Nicandra physalodes; Nicotiana benthamiana; Nicotiana clevelandii; Nicotiana glutinosa; Nicotiana rustica; Nicotiana sylvestris; Nicotiana tabacum; Nicotiana edwardsonii; Ocimum basilicum; Petunia hybrida; Phaseolus vulgaris; Phytolacca americana; Pisum sativum; Raphanus sativus; Ricinus communis; Salvia splendens; Senecio vulgaris; Solanum melongena; Solanum nigrum; Solanum tuberosum; Spinacia oleracea; Stellaria media; *Trifolium pratense; Trifolium repens; Tropaeolum majus; Tulipa; Vicia faba; Vicia villosa; Viola arvensis*.

Target genes include those which confer 'unwanted' traits in the plant and which it may therefore be desired to silence using VIGS. Examples include ripening specific genes in tomato to improve processing and handling characteristics of the harvested fruit; genes involved in pollen formation so that breeders can reproducibly generate male sterile plants for the production of F1 hybrids; genes involved in lignin biosynthesis to improve the quality of paper pulp made from vegetative tissue of the plant; gene silencing of genes involved in flower pigment production to produce novel flower colours; gene silencing of genes involved in regulatory pathways controlling development or environmental responses to produce plants with novel growth habit or (for example) disease resistance; elimination of toxic secondary metabolites by gene silencing of genes required for toxin production.

A further aspect provides a process which includes introducing the vector into a plant, optionally including the further step of introducing a source of proteins encoded by TRV RNA1 into the plant.

A further aspect of the present invention provides a method which includes causing or allowing transcription from a construct as disclosed within the genome of a plant cell to produce a cytoplasmically-replicating RNA.

A further aspect of the present invention provides a method of reducing or suppressing or lowering the level of a target gene in a plant cell, the method including causing or allowing transcription from a vector as disclosed above.

In preferred forms the present invention is concerned with providing VIGS-based methods are useful in functional genomics. Thus in one aspect of the present invention, the target gene may be of unknown phenotype, in which case the VIGS system may be employed to analyse the phenotype by generating a widespread null (or nearly null) phenotype. The target gene may be essential, which is to say that the null phenotype is lethal to the cell or tissue in question.

This aspect of the invention may comprise a method of characterising a target gene comprising the steps of:
(a) silencing the target gene in a part or at a certain development stage of the plant using the TRV VIGS system described above,
(b) observing the phenotype of the part of the plant in which or when the target gene has been silenced.

Generally the observation will be contrasted with a plant wherein the target gene is being expressed in order to characterise (i.e. establish one or more phenotypic characteristics of) the gene.

The advantage of the TRV system over certain prior art constructs is discussed above. There are also several advantages of the current method over alternative methods in which the targeted gene is inactivated by insertional or other mutagenic procedures. The advantage over mutagenic procedures applies when there is more than one homologous gene carrying out the role of the target gene. Mutagenic procedures will not normally reveal a phenotype in that situation. A second situation where the current invention has advantage over both mutagenic and unregulated gene silencing procedures applies when the target gene has a lethal phenotype. The controllable attribute of the gene silencing will allow the phenotype of such genes to be investigated and exploited more efficiently than using the alternative methods available prior to the disclosure of the current invention.

Nor, for the identification of endogenous genes, would it be necessary to try and generate a transgenic plant in which gene silencing is already activated to observe the effect.

In a further aspect there is disclosed a method of altering the phenotype of a plant comprising use of the silencing method discussed above. Traits for which it may be desirable to change the phenotype include the following: colour; disease or pest resistance; ripening potential; male sterility.

In a further aspect of the present invention there is disclosed a virus or viral particle including, preferably encapsulating, a vector (or transcript from the expression cassette in the vector) according to the present invention.

In a further aspect of the present invention there is disclosed a kit comprising a vector as described above, plus a source of TRV RNA1 polypeptide or vector encoding the same (e.g. pBINTRA6).

In a further aspect of the present invention there is disclosed a host cell including a vector according to the present invention. These may be plant cells, or may be microbial (particularly bacterial and especially Agrobacterium) cells.

In a further aspect there is disclosed a plant, or plant tissue, including, or transiently transformed by, a vector of the present invention.

The invention will now be further described with reference to the following non-limiting Figures and Examples. Other embodiments of the invention will occur to those skilled in the art in the light of these.

FIGURES

FIG. 1; Schematic illustration of the cloning steps to produce pTV00. 35S is the CaMV 35S promoter; 37K and 32.8K are the open reading frames for the 37K and 32.8K proteins; UTR is the untranslated region; Nos is the nopaline synthase transcriptional terminator; RB is the right border; LB is the left border.

FIGS. 2A–2B A; Schematic drawing of TRV RNA1; 5' UTR and 3' UTR are the 5' and 3' untranslated regions respectively; Rep 134 K is the 134 KDa replicase protein; Rep 194 K is the 194 KDa read-through replicase protein; MP is the movement protein; 16 K is the 16 KDa protein. B; The relative positions of the PCR1 and PCR2 cDNA fragments.

Figure 3:
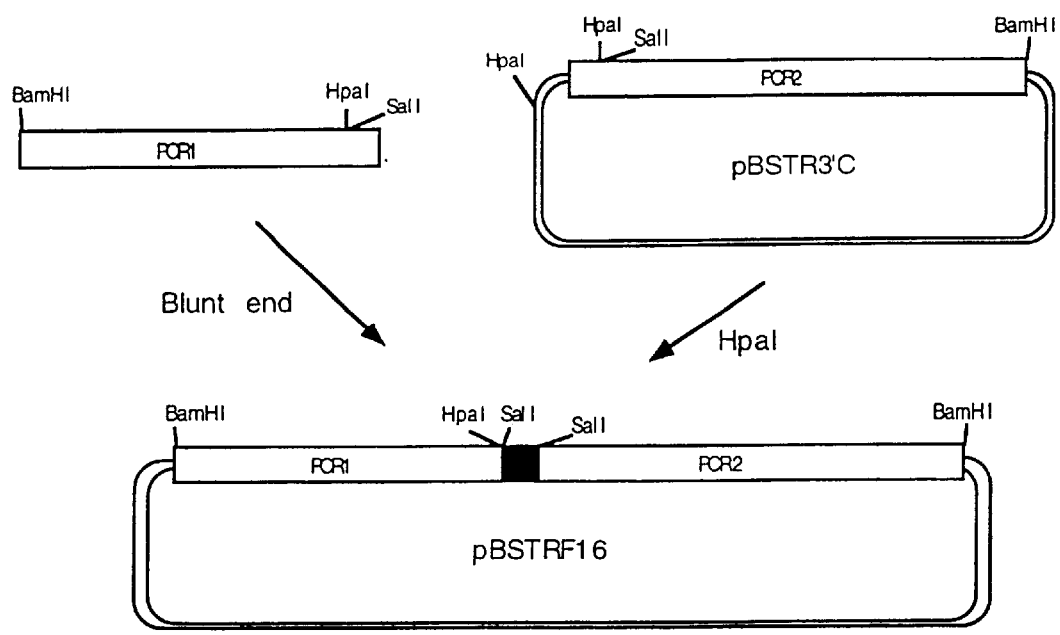

FIG. 3. Schematic illustration of the cloning strategy for pBSTRF16.

Figure 4:
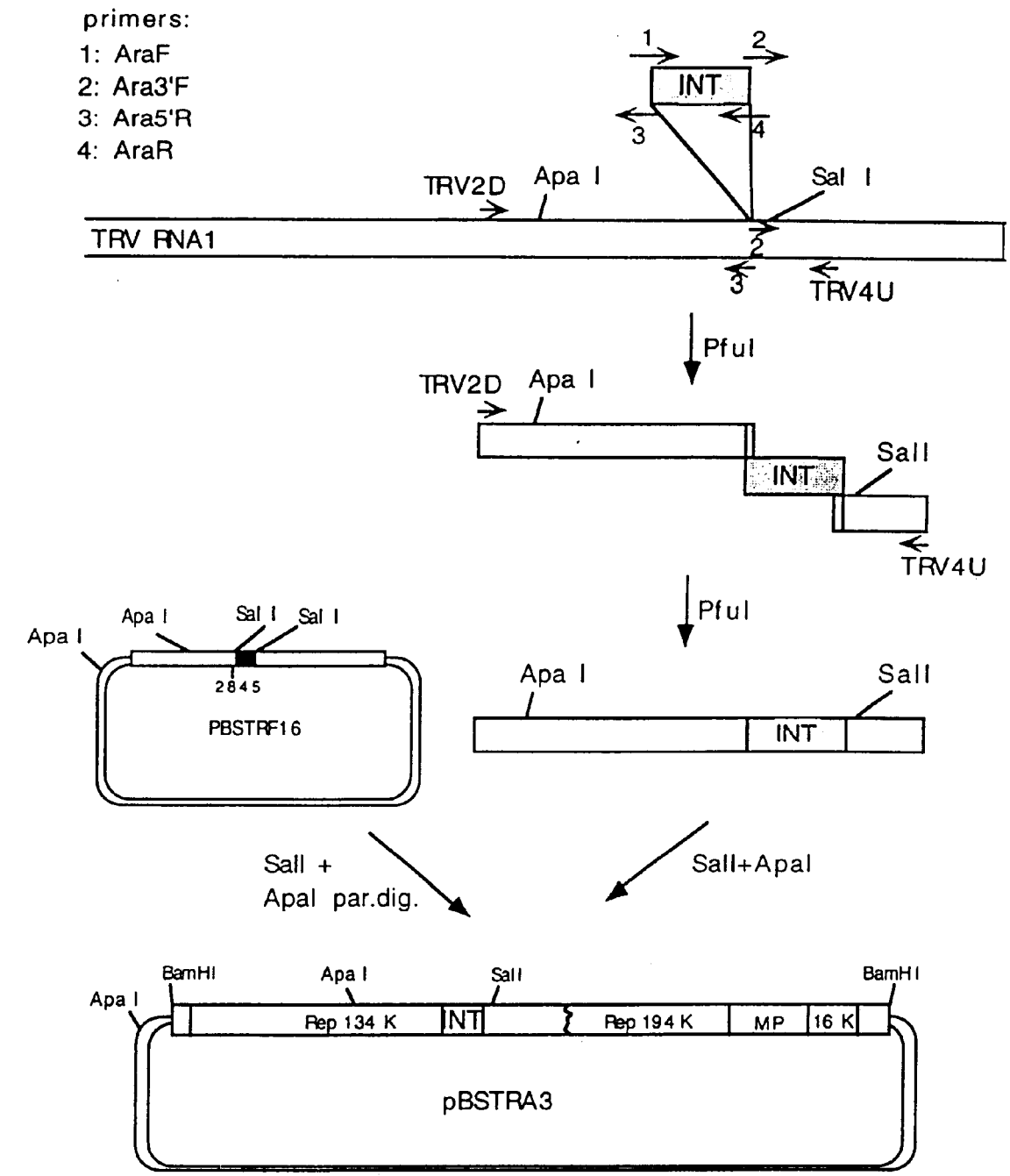

FIG. 4. Schematic representation of the cloning strategy for the introduction of intron 3 from *A. thaliana* NIA1 gene to TRV RNA 1, to obtain pBSTRA3. INT is NIA1 gene intron 3.

Figure 5:
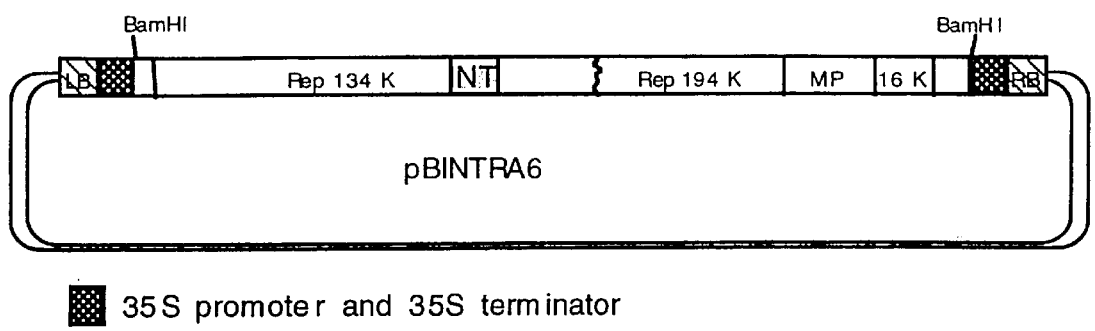

FIG. 5. Schematic representation of pBINTRA6. LB and RB respectively are the left border and right border of pBINTRA6 T-DNA.

SEQUENCE APPENDICES

1. The full sequence of pTV00.
2. PEBV promoter sequence.
3. *N. benthamiana* pds cDNA fragment.
4. *A. thaliana* pds cDNA fragment.
5. *N. benthamiana* rubisco cDNA fragment.
6. GFP (PCR amplified).
7. *N. benthamiana* NFL cDNA fragment.
8. The full sequence of pBINTRA6.

EXAMPLES

General Materials and Methods

All DNA modifications and digestions were performed using enzymes according to the manufacturers' instructs and following protocols described by Sambrook et al. (Sambrook, Fritsch et al. 1989).

The TRV vector PTV00 was derived from pCaK20-2T7, a previously described clone of TRV RNA2 (Hernandez, Mathis et al. 1995). pCaK20-2T7 contains a full-length cDNA of TRV strain PPK20 RNA2 cloned between the cauliflower mosaic virus (CaMV) 35S promoter and the Nos terminator.

For the construction of pTV00 two fragments of pCaK20-2T7 were cloned into the binary plant transformation vector pGreen0000 (described below). The first fragment, of 1536 bp, included the CaMV 35S promoter, and cDNA sequence encoding the TRV RNA2 5' untranslated region and coat protein. This fragment was released by digesting pCaK20-2T7 with Bgl II, treating with T4 DNA polymerase, and subsequently digesting with Sac II. The resulting fragment was ligated into the binary plasmid pGreen 0000 that had been cut with Xba I, blunted with T4 DNA polymerase and digested with Sac II, to form the plasmid pGreen35Sorf1.

The second fragment of pCaK20-2T7, containing the 3' untranslated region (UTR) of TRV RNA2 and the Nos terminator, was released by digestion with BbsI and FspI and then blunted with T4 DNA polymerase. This 835 bp fragment was ligated into pGreen35Sorf1 at an Fsp I site, to form pTV00. The full sequence of pTV00 is given in Appendix 1. A schematic illustration of the cloning procedure is shown in FIG. 1.

These cloning steps had three purposes. Firstly, the TRV RNA 2 cDNA clone was introduced to the T-DNA of a plant binary-transformation vector. This allows Agrobacterium mediated-infection of TRV RNA 2 without the need for in vitro transcription as previously described for another TRV RNA2 clone (Ratcliff, MacFarlane et al. 1999). The second effect of these cloning steps was to remove the cDNA sequences that encode the 37K and 32.8K proteins. These proteins are dispensable for TRV infection, and are required for transmission of TRV by nematode vectors (MacFarlane 1999). The third effect was to introduce 12 unique restriction enzyme sites into the genome of the TRV RNA 2. This multiple cloning site (MCS) is more convenient for the insertion of novel sequences to TRV RNA 2 than the single restriction enzyme site present in the previously described TRV RNA 2 vector (Ratcliff, MacFarlane et al. 1999).

A 409 bp cDNA fragment of pds was PCR amplified from *N. benthamiana* cDNA using Taq DNA polymerase and the primers 5' ggcactcaactttataaacc and 5' cttcagttttctgtcaaacc. This pds cDNA fragment (Appendix 3) was cloned into the Sma 1 sites of pTV00 and into pGR107, to form pTV.pds and pGR107. pds respectively.

For construction of pTV.apds a 1.7 kb fragment of the pds gene was PCR amplified from *A. thaliana* cDNA using Taq DNA polymerase and the primers 5' cccctcgagagatgtcaaatc (SEQ ID No: 3) and 5' cccctcgaggcactttcatctgg (SEQ ID No: 4). This *A. thaliana* pds cDNA fragment (Appendix 4) was cloned into pTV00 at the Sma 1 site.

A 500 bp cDNA fragment of the rubisco small sub-unit was PCR amplified from *N. benthamiana* cDNA using Taq DNA polymerase and the primers 5' cagtctagatggcttcctcagt-tctttcc (SEQ ID No: 5) and 5' cagggatcccacttgacgcacgttgtc (SEQ ID No: 6). This rubisco cDNA fragment (Appendix 5) was cloned into the Sma 1 sites of PTV00 and pGR107 to form pTV.rubisco and pGR107.rubisco respectively.

A 321 bp fragment corresponding to the 3' end of GFP (designated P) was PCR amplified using Taq DNA polymerase and the primers 5' aacatcctcggcccacaagtt (SEQ ID No: 5) and 5' gagctcttagagttcgtcatg(SEQ ID No: 8). This fragment (Appendix 6) was cloned into the Sma 1 sites of pGR107 and pTV00 to form pGR107.P and pTV.P respectively.

421 bp cDNA fragment of the NFL gene was PCR amplified from *N. benthamiana* using Taq DNA polymerase and the primers 5' tggacccagaggctttctc (SEQ ID No: 9) and 5' cttcttgtgagagagcgtca (SEQ ID No: 10). This NFL cDNA fragment (Appendix 7) was cloned into pGR107 and pTV00 at the Sma 1 sites to form pGR107.NFL and pTV.NFL respectively.

pBINTRA6, a full length infectious clone of TRV (strain PPK20) RNA1, was constructed as follows.

Figure 2:
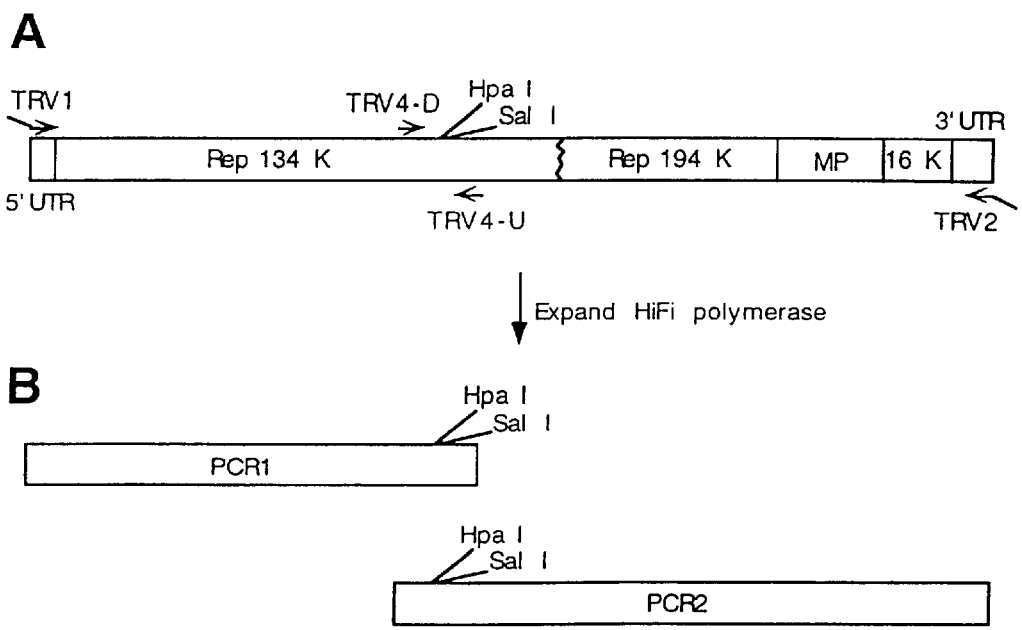

Total RNA was prepared from TRV (strain ppk20) infected *N. benthamiana* plants as previously described (Devic, Jaegle et al. 1989). Full length cDNA corresponding to TRV RNA1 was prepared from this RNA using Superscript Reverse Transcriptase (Gibco) and the primer TRV2 5' gggggatccgggcgtaataacgcttacg3' (SEQ ID No: 11) which anneals to the 3' end of TRV RNA1. A schematic drawing of TRV RNA1 is shown in FIG. 2. All primers in this work were derived from the sequence of a closely related TRV strain SYM (Hamilton, Boccara et al. 1987) The full-length cDNA was used as a template for PCR amplification of two overlapping fragments, PCR1 and PCR2, which together cover all of TRV RNA1.

PCR1, a 3.2 kb fragment, was amplified using Expand HiFi polymerase (Roche). The primers were: TRV1 ' ggggg-gatccataaaacatttcaatcctttg3' (SEQ ID No: 12) (which anneals to positions 1–21 of TRV) and TRV4U 5' ttagcaccagctatct-gagcgc3' (SEQ ID No: 13) positions 3168–3189). PCR2, a 4.1 kb product, was also amplified using Expand HiFi polymerase (Roche) and the primers TRV4D 5' gttccaacca-gacaaacgtatgg3' (SEQ ID No: 14) (positions 2698–2720) and TRV2 (see above).

PCR1 and PCR2 share a 491nt overlap in the replicase open reading frame (ORF). The primers TRV1 and TRV2 contain BamHI sites to allow cloning of the full-length product (FIG. 2). PCR2 was blunt-ended using T4 DNA polymerase, digested with BamHI, and cloned into the plasmid pBAC/SacBl (Bendahmane, Kanyuka et al. 1999) which had previously digested with BamHI and EheI to form pBSTR3' C. The PCR1 fragment was blunted-ended with T4 DNA polymerase and ligated into HpaI digested-pBSTR3' C, to form pBSTRF16 (FIG. 3). pBSTRF16 therefore contains 302 bp that are duplicated within the replicase ORF.

The 302 bp of duplicated replicase sequence was replaced with a 438 bp intron. Intron 3 of *Arabidopsis thaliana* Col-0 nitrate reductase NIA1 gene (Wilkinson and Crawford 1993) was amplified using the primers AraF and AraR. AraF is 5' CGTATCTTTGCAA TAACAGgtaataatcctctctcttgatatt3' (SEQ ID No: 15) where the sequence in upper case corresponds to positions 2826–2845 of TRV RNA1 and the sequence in lower case corresponds to positions 1–24 of the intron. Similarly, AraR is 5' TTAAATTGTCCAAGAT-CAACct gtttaacacaagtcaacgtc3' (SEQ ID No: 16) where the sequence in upper case corresponds to positions 2846–2864 of TRV RNA 1 and the sequence in lower case corresponds to positions 416–438 of the intron. The PCR amplified intron 3 fragment was therefore flanked by the AGGT intron splice,sites, and 19 bp of TRV (exon) sequence (FIG. 4). Two TRV-exons (exon 1 and exon 2) that flank the intron insertion site were then PCR amplified. For exon 1 the primers were TRV2D 5' tcgcacaaaaccaaggtgatag3' (SEQ ID No: 17) (positions 1772–1793) and Ara5' R 5' ggattatt acCTGTTATTGCAAAGATACGTCTG3' (SEQ ID No: 18) where the sequence in lower case corresponds to positions 1–10 of the intron and sequence in upper case corresponds to positions 2822–2845 of TRV RNA1. Exon 1 was amplified as a 107 kb fragment from pBSTR16. For exon 2 the primers were Ara3' F 5' tgttaaacagGTTGATC TTGGA-CAATTTAAGTGC3' (SEQ ID No: 19), where the sequence in upper case corresponds to positions 2846–2868 of TRV RNA1 and the sequence in lower case corresponds to positions 428–438 of the intron, and TRV4U (see above). Exon 2 was amplified as a 0.35 kb fragment from PCR 1 (see above). Exon 1, intron 3 and exon 2 were all amplifed using Pfu polymerase (Promega). To introduce intron 3 to the TRV RNA 1 genome, chimeric PCR was performed with Pfu polymerase and the primers TRV2D and TRV4U using a mixture of exon 1, intron 3 and exon 2 as template to give a 1.8 kb fragment.

This 1.8 kb intron-containing-fragment was digested with ApaI and SalI and cloned in pBSTRF16 using ApaI-partial digestion and SalI, thus replacing the region that included duplicated sequence, and forming pBSTRA3 (FIG. 4).

To transfer the cloned RNA1 to a binary transformation vector, the 7.2 kb fragment corresponding to TRV RNA 1 was released from pBSTRA3 with BamHI and cloned into the BamHI site between the CaMV 35s promoter and the CaMV terminator on the plasmid pBIN61 to form pBIN-TRA6 (FIG. 5). pBIN61 is a modified version of the pBIN19 (Frisch, Harris-Haller et al. 1995) binary vector that carries a transcription cassette comprising the CaMV 35S promoter and terminator. To construct the pBIN61 binary vector, the transcription cassette containing the CaMV 35S promoter and terminator was released by digestion with KpnI and XhoI from the plasmid pJIT61 (kindly provided by P. Mullineaux, JIC, Norwich, UK). The transcription cassette was then ligated to the pBIN19 plasmid vector digested with KpnI and SalI to create pBIN61.

Agrobacterium strain GV3101 containing pBINTRA6 was infiltrated into N. benthamiana leaves causing a TRV RNA 1 infection. The full sequence of pBINTRA6 is given in Appendix 8.

The kanamycin resistance gene (NptI) from pACYC177 (Chang and Cohen 1978) was cloned as a NheI-NcoI fragment into the SpeI-BspHI sites of pBluescript SKII+, creating intermediate I. The NcoI site was introduced and restriction sites that would have been duplicated in the pGreen polylinker were removed by site-directed mutagenesis (mutagenic oligos: XhoI (5' cgtcttgctcaaggccgcgat 3'(SEQ ID No: 20)). ClaI (5' cgacaatcta ccgattgtatg 3' (SEQ ID No: 21)), SmaI (5' ctgcgatcccagggaaaacag 3' (SEQ ID No: 22)) HindIII (5' aaatgcataaagtttt gccat 3' (SEQ ID No: 23)) and NcoI (5' tggttgtaaccatggcagagca 3' (SEQ ID No: 24). Two complementary oligos (5' gaattcagatcta3' and 5' acatgtagatctg3' (SEQ ID No: 24) respecively ) were annealed and inserted between the EcoRI and AflIII sites, to introduce a unique BglII site, this was intermediate II. The psa-ori sequence from pJIT134Sa-Bam was inserted as a BamHI-SmaI fragment into the BamHI-SmaI sites (remaining from the original pBluescript plasmid) of intermediate II. These sites, along with intervening PstI and NotI sites were removed by successive rounds of treatment with T4 DNA polymerase I (T4 polI) and re-ligation. The StuI site in the NptI promoter and ClaI sites, introduced when the psa-ori was inserted, were removed by transformation into E. coli strain SCS110 (dam;dcm), digestion with T4 polI and re-ligation. This produced the pGreen backbone that was ready to receive the T-DNA cassette.

The complementary olignucleotides (5'-cataaggccttgacaggatatattggcgggtaaactaa gtcgctgtatgtgtttgtttgagatct-3' (SEQ ID No: 27) and 5'-catgagatctcaaacaaacacatacagcgacttagtttacccg ccaatatatcctgtcaaggcctt-3' (SEQ ID No: 28)) were annealed to produce a DNA fragment consisting of a StuI site, the RB sequence, the RB "overdrive" sequence and a BglII site. This RB DNA fragment was inserted into the AflIII site of pBluescript SKII- and its orientation determined by sequencing. A recombinant plasmid (intermediate A) was selected which had the orientation of the RB fragment such that the StuI site was nearest to the SK multiple cloning site.

Two further oligonucleotides (5'-tccacacattatacgagccgatgattaattgtcaacagatcttggcag gatatattgtggtgtaaacgttaac-3(SEQ ID No: 29) and 5'-ggtaacgtttacaccacaatatatcctgccaagatctgttgacaatta atcatcggctcgtataatgtgtgga-3' (SEQ ID No: 30)) were then annealed to produce an LB DNA fragment consisting of HpaI and BglII site and LB sequence. This fragment was inserted between the two SspI sites of intermediate A, simultaneously deleting the pBluescript SKII- f1 ori. This 815 bp BglII fragment was cloned into the pGreen backbone to produce pGreen0000.

All work involving virus infected material was carried out in containment glasshouses under MAFF license PHF 1420c/1773(12/1996). N. benthamiana and A. thaliana plants were germinated on a 1:1 mixture of JIC compost and peat, then grown individually in pots at 25° C. during the day and 20° C. during the night. Supplementary winter lighting from halogen quartz iodide lamps provided a 16 hour day length.

Virus infections on N. benthamiana were achieved by Agrobacterium-mediated transient gene expression of infectious constructs from the T-DNA of a binary plasmid (e.g. pGR107, pTV00 or PBINTRA6). Agrobacterium was grown to an OD of 600 in L broth. The culture was then centrifuged and re-suspended in 10 mM MgCl12, 10 mM MES and 150 mM acetosyringone, and kept at room temperature for 2 hours. The culture was then infiltrated to the underside of a leaf using a 2 ml syringe without a needle.

For virus infections on A. thaliana, Agrobacterium cultures carrying pBINTRA6 and pTV.apds were first infiltrated to N. benthamiana, as described above. A week later, systemically infected leaves were ground in 50 mM phosphate buffer pH7 using a pestle and mortar. The solution was then centrifuged for 1 minute at 3000 rpm and the supernatant was rubbed onto the leaves of carborundum-dusted plants.

For RNA infection, total RNA was purified from infected plants as previously described (Devic, Jaegle et al. 1989). 5 m of this RNA was rubbed onto the leaves of carborundum dusted plants.

Total RNA from N. benthamiana was prepared using Tri-reagent (Sigma). Genomic DNA was removed from this RNA by incubation with DNase (Sigma) at 37° C. for 2 hours followed by phenol extraction. This RNA was used as a template for first-strand cDNA synthesis using random hexanucleotide primers and Super-Script Reverse Transcriptase (Roche) according to the manufacture's instructions. This cDNA was diluted 2000 fold in sterile distilled water, and used as a template for quantitative PCR in an ABI Prism 7700 Sequence Detection System (PE Applied Biosystems) with 2xTaqman Universal PCR Mastermix (PE Applied Biosystems). For rubisco amplification, the primer sequences were cgtcaagtgcagtgcatcagt (SEQ ID No: 34 and gacaatagggtaagttgtcctaatatgaaa (SEQ ID No: 32) and the probe sequence was cattgcctccaagcctgacgga (SEQ ID No: 33). Each sample was quantitatively standardised by amplification of 25S ribosomal cDNA using the primers acca-cagggataactggcttgt (SEQ ID No: 34) and ccgacatcgaaggat-caaaaa (SEQ ID No: 35) with the probe cagccaagcgtcatagcgacgttg(SEQ ID No: 36). The probe DNA was modified to contain 5' FAM fluorescent reporter and 3' Tamra quencher (MGW). To confirm that PCR amplification corresponded to mRNA levels and not from genomic or contaminating DNA, additional reactions were performed without template cDNA and with RNA that had not been treated with reverse-transcriptase.

Example 1

Comparison of Silencing of Pds Gene by TRV and PVX VIGS Vectors

To assess whether constructs derived from TRV have advantages over previously described virus vectors, we compared symptoms and VIGS caused by TRV and another virus. PVX was used for this comparison, because it inhibits expression of a wide range of plant genes (Ruiz, Voinnet et al. 1998; Jones, Hamilton et al. 1999). Furthermore, as with TRV, an infectious PVX cDNA construct is available under control of the CaMV 35s promoter on the binary transformation plasmid "pGreen" (pGR107, (Jones, Hamilton et al. 1999)). As both TRV and PVX derivatives are therefore introduced to plants in the same way, any differences can be attributed to the virus itself, rather than the means of inoculation.

We next compared the ability of TRV and PVX derived constructs to inhibit plant gene expression in N. benthamiana. Identical plant cDNA sequences were inserted into pTV00 and pGR107 to compare the efficiency of TRV and PVX at silencing the same plant gene. cDNA sequences from two plant genes were used for this comparison.

The first cDNA we used was part of the phytoene desaturase (pds) gene. Pds is essential for production of carotenoids that protect plants from photobleaching (Demmig-Adams and Adams 1992). Plant tissue in which pds is inhibited therefore turns white due to photobleaching. This whitening phenotype provides a useful visual marker for assessing the extent and severity of VIGS (Kumagai, Donson et al. 1995; Ruiz, Voinnet et al. 1998). A further rationale for choosing pds as a target of VIGS is that the copy number and expression level of the pds gene is low (Ruiz, Voinnet et al. 1998). VIGS of pds therefore indicates the potential of a virus to inhibit the expression of a low abundance mRNA. For these experiments a 409 bp cDNA fragment of pds (Appendix 3) was PCR amplified from *N. benthamiana* cDNA and cloned in the sense orientation into pTV00 and pGR107, to form pTV.pds and pGR107.pds respectively.

Leaves of 3 week old *N. benthamiana* plants were infiltrated with Agrobacterium containing either pGR107.pds, to cause PVX.pds infections, or with Agrobacterium containing pBINTRA6 and pTV.pds, to cause TRV.pds infections. As previously reported (Ruiz, Voinnet et al. 1998), after 3 weeks plants infected with PVXpds developed symptoms of photobleaching that are typical of pds inhibition. Stems, axillary shoots, and sepals were affected. In leaves the photobleaching was initiated and predominantly maintained around the veins. However, a large proportion of the leaf surface remained green. Plants infected with TRV.pds also developed photobleaching symptoms. Again, stem, axillary shoots, sepals and leaves were affected. However, unlike leaves infected with PVX.pds, leaves infected with TRV.pds became predominantly white, indicating widespread silencing of pds gene by the TRV based construct.

These data are typical of 10 repeats, and show that when TRV and PVX derivatives carry the same fragment of the pds gene, the TRV construct inhibits pds activity in a higher proportion of leaf tissue than the PVX vector.

Example 2

Comparison of Silencing of Rubisco by TRV and PVX VIGS Vectors

A second comparison of VIGS caused by TRV and PVX was made using the small sub-unit of ribulose -1,5-bisphosphate carobxylase oxygenase (rubisco). Antisense or PVX.rubisco induced inhibition of rubisco causes chlorotic and stunting symptoms (Rodermel, Abbott et al. 1988; Jones, Hamilton et al. 1999). A further rationale for choosing rubisco as a target of VIGS is that the copy number and expression level of the rubisco genes is very high. In contrast to pds, VIGS of rubisco would therefore indicate the potential of a virus to inhibit the expression of a high abundance endogenous mRNA. A 500 bp cDNA fragment of the rubisco small sub-unit (Appendix 4) was PCR amplified from *N. benthamiana* cDNA and cloned in the sense orientation into pTV00 and pGR107 to form pTV.rubisco and pGR107.rubisco respectively.

Leaves of 3 week old *N. benthamiana* plants were infiltrated either with Agrobacterium containing pGR107.rubisco, to cause a PVX.rubisco infection, or with Agrobacterium containing pEINTRA6 and pTV.rubisco, to cause a TRV.rubisco infection.

Three weeks after infiltration, the upper leaves of plants that were infected with PVX.rubisco developed very pale green or yellow patches. However, as with PVX induced inhibition of pds, leaves were not uniformly affected. Similar areas of pale green developed on stems, axillary shoots and sepals. These pale green areas were distinct and different from the mosaic normally associated with PVX infection. Plants that were infected with TRV.rubisco also developed pale green or yellow tissue in systemically infected leaves, stems, axillary shoots and sepals. However, in contrast to PVX.rubisco infected plants, in TRV.rubisco infected leaves there was no mosaic, and the pale green or yellow symptoms appeared uniform across the leaf. This experiment was repeated more than 10 times, with the same result.

To confirm that the symptoms associated with PVX.rubisco and TRV.rubisco infection were caused by inhibition of rubisco, and to quantify any reduction in rubisco mRNA caused by each construct, rubisco mRNA levels were measured by Taqman PCR (PE Applied Biosystems). In these experiments, total RNA from infected plants was used as a template for first-strand cDNA synthesis. Quantitative PCR was then used to assess the ratio of rubisco cDNA to that of ribosomal cDNA in PVX.rubisco or TRV.rubisco infected plants, and in uninfected plants. The rubisco sequence carried by the PVX and TRV constructs was not PCR amplified in these experiments as the primers used were outside the region carried by in the virus vectors (see Materials and Methods). Nine separate plants were used for each treatment, and each plant was analysed three times.

In leaves infected with PVX.rubisco there was a 37 fold reduction in rubisco mRNA compared to the levels in mock inoculated plants (Student's T-Test; $P=1.96 \times 10^{-7}$). However, in leaves infected with TRV.rubisco there was an even greater reduction in rub sco levels of 200 fold compared to mock inoculated plants ($P=2.1 \times 10^{-7}$). These data show that the TRV based construct is 5.4 ($P=0.02$) fold more efficient at suppressing rubisco accumulation than the PVX based construct carrying an identical rubisco sequence.

Example 3

Comparison of Silencing in *A. thaliana* by TRV and PVX VIGS Vectors

One disadvantage of currently available virus vectors is that they have a limited host range. For example, neither PVX nor TMV vectors infect the model plant *A. thaliana*. In an attempt to overcome this limited host range, some authors have made transgenic *A. thaliana* plants that express a full-length infectious PVX cDNA carrying endogenous plant gene sequence. This strategy was pursued because PVX replicates in *A. thaliana* protoplasts, but does not infect whole plants. However, even when PVX is expressed from a transgene and replicating in every cell, there was little or no inhibition of homologous Arabidopsis gene expression (unpublished data).

We tested whether constructs based on TRV would inhibit gene expression in *A. thaliana*. A fragment of the pds gene was PCR amplified from *A. thaliana* cDNA (Appendix 5) and cloned the sense orientation into pTV00 to form pTV.apds. No TRV infections could be established by infiltrating *A. thaliana* with Agrobacterium carrying pBINTRA6 and pTV.pds or pTV00. Therefore, TRV.apds infections were established by infiltrating Agrobacterium that contained pBINTRA6 and pTV.apds to *N. benthamiana*. Infectious sap from these *N. benthamiana* plants was subsequently used to inoculate *A. thaliana* ecotype Col-0 (see Materials and Methods). As with *N. benthamiana*, *A. thaliana* plants infected with TRV developed no symptoms. However, *A. thaliana* plants infected with TRV.apds developed confluent photobleaching in systemic leaves that is typical of pds inhibition. These data suggest that unlike PVX, TRV can inhibit gene expression in a range of plant species including *A. thaliana*.

Example 4

Comparison of Silencing of GFP Transgene in Meristematic Tissue by TRV and PVX VIGS Vectors A sub-set of genes that control identity and development of newly forming plant tissues are expressed in meristematic regions. Understanding the function of these genes is of particular interest as they determine characteristics such as fruit and flower production. However, PVX, TMV and TGMV do not infect meristems (Matthews 1991), and therefore cannot be used to inhibit meristem-expressed genes.

We assessed whether our TRV based vector would overcome this limitation by comparing the ability of the PVX and TRV derived constructs to inhibit the expression of two genes in meristems. The first of these genes encodes the green fluorescent protein, GFP (Chalfie, Tu et al. 1994). A 321 bp fragment corresponding to the 3' end of GFP (designated P; Appendix 6) was PCR amplified and cloned in the sense orientation into pGR107 and pTV00 to form pGR107.P and pTV.P respectively. For these experiments *N. benthamiana* plants were used that express GFP from a CaMV 35s driven transgene (line 16c, (Ruiz, Voinnet et al. 1998)). In UV light these plants-fluoresce green due to expression of the GFP transgene. In contrast, non-transgenic plants, and 16c plants in which GFP expression is inhibited, are red under UV illumination, due to fluorescence from chlorophyll.

Three week old 16c *N. benthamiana* plants were infiltrated with Agrobacterium containing either pGR107.P, to cause a PVX.P infection, or pBINTRA6 and PTV.P to cause a TRV.P infection, or with water. As previously reported, 3 weeks after infiltration the leaves, stems and axillary shoots of plants infected with PVX.P had lost all green fluorescence, and appeared red under UV light (FIG. 5A) (Ruiz, Voinnet et al. 1998). Similarly, 16c plants that were infected with TRV.P also lost GFP expression in leaves, stems and axillary shoots. We then assessed the level of GFP expression in vegitative meristematic regions using confocal laser-scanning microscopy. As previously reported (Ruiz, Voinnet et al. 1998) PVX.P did not inhibit GFP expression in this region, as the meristem and surrounding leaf primordia in these plants remained green-fluorescent. In contrast, TRV.P inhibited GFP expression in the meristematic dome and surrounding leaf primordia.

Example 5
Comparison of Silencing of LFY Endogenous Gene in Meristematic Tissue by TRV and PVX VIGS Vectors We next compared the ability of PVX and TRV derived constructs to inhibit the expression of an endogenous gene in meristems. The gene we chose was NFL, the Nicotiana floricola homologue of the *A. thaliana* gene leafy (LFY). LFY is important for determination of floral organs. *A. thaliana* lfy mutants have two characteristics; additional inflorescence shoots are formed in the place of early flowers, and flowers that develop later are abnormal and contain shoot-inflorescence tissue (Weigel, Alvarez et al. 1992). We therefore predicted that inhibiting NFL expression would have similar effects on flower formation in *N. benthamiana*. A 421 bp cDNA fragment of the NFL gene was PCR amplified from *N. benthamiana* cDNA (Appendix 7) and cloned into in the sense orientation into pGR107 and pTV00 to form pGR107.NFL and pTV.NFL respectively.

Three week-old *N. benthamiana* plants were infiltrated with water (mock), or with Agrobacterium containing pGR107 or pGR107.NFL to cause PVX or PVX.NFL infections, or pBINTRA6 and PTV00 or pTV.NFL to cause a TRV or TRV.NFL infections respectively. Six plants were used for each treatment. The arrangement and formation of leaves, flowers and branches was recorded after 12 weeks. In *N. benthamiana*, organs are formed at nodes around the main stem. Each node typically consists of a leaf, a primary branch, and a flower. The branches vary in size and complexity, and may give rise to secondary, or occasionally tertiary branches, before producing flowers. Floral organs such as petals, sigma and stamen are formed after a whorl of leaves known as sepals. On each plant, the number of primary, secondary and tertiary branches was recorded, as well as the number of correct and incorrectly formed flowers. Although there was structural variation between plants, there were no consistent changes between mock inoculated plants, and plants that were infected with PVX, PVX.NFL or TRV. All plants produced secondary branches. One TRV and one PVX.NFL infected plant each produced a single tertiary branch. All flowers on these plants were normal compared to mock inoculated plants. In contrast, plants infected with TRV.NFL had a more complex and branched structure. Each of these plants produced secondary and tertiary branches. Five of the six plants also produced quartenary branches. These additional branches were formed in place of flowers. Many of the flowers that were formed on TRV.NFL infected plants were abnormal. Flower defects ranged from repeated whorls of sepals, to floral structures containing single or multiple inflorescence branches which themselves gave rise to more floral structures. These data are reminiscent of floral abnormalities in Arabidopsis lfy mutants, and are entirely consistent with an inhibition of NFL expression in the meristematic regions of *N. benthamiana*.

Taken together, these two experiments with GFP and NFL show that unlike other viral vectors, constructs based on TRV can inhibit gene expression in meristems.

Example 6
TRV as an Expression Vector

The TRV derived virus vector PTV00 has been specifically designed to inhibit rather than direct protein synthesis. For certain purposes it may be advantageous to modify PTV00 to allow protein expression from this vector. If the multiple cloning site of pTV00 was immediately preceded by a sub-genomic promoter that was recognised by the replicase protein of TRV RNA 1, then proteins would be translated from a sub-genomic RNA.

For example, total RNA could be prepared from PEBV infected *N. benthamiana* plants as previously described (Devic, Jaegle et al. 1989). cDNA corresponding to the coat protein sub-genomic promoter of PEBV could be prepared and then PCR amplified from this total RNA using Superscript Reverse Transcriptase (Gibco) followed by Pfu polymerase (Promega) with the primers ggatccgcacacaaggtta and gggcgcgccctcgttaac. This PEBV sub-genomic promoter cDNA fragment (Appendix 2) could be cloned into pTV00 that was previously digested with Spe 1 and blunted with T4 DNA polymerase, to form pTV1.0. Open reading frames cloned in sense and in frame in the remainder of the multiple cloning site would then be expressed. For example, GFP cDNA sequence (Chalfie, Tu et al. 1994), could be inserted into the BamHi 35 site, to achieve GFP expression in any host plant such as *N. benthamiana*.

References

Inasmuch as they may be required by the person skilled in the art to practice the present invention, all citations are specifically included herein by cross-reference.

Al-Kaff, N. S., S. N. Covey, et al. (1998). "Transcriptional and post-transcriptional plant gene silencing in response to a pathogen." *Science* 279: 2113–2115.

Bendahmane, A., K. Kanyuka, et al. (1999). "The Rx gene from potato controls separate virus resistance and cell death responses." *Plant Cell* 11: 781–791.

Chalfie, M., Y. Tu, et al. (1994). "Green fluorescent protein as a marker for gene expression." *Science* 263:

802–805. Chang, A. C. Y. and S. N. Cohen (1978). "Construction and characterisation of amplifiable multicopy DNA cloning vehicles derived from the P15A cryptic miniplasmid." *Journal of Bacteriology* 134: 1141–1156.

Covey, S. N., N. S. Al-Kaff, et al. (1997). "Plants combat infection by gene silencing." Nature 385: 781–782.

Demmig-Adams, B. and W. W. Adams (1992). "Photoprotection and other responses of plants to high light stress." "Annu.Rev.Plant Physiol.Plant Mol.Biol. 43: 599–626.

Devic, M., M. Jaegle, et al. (1989). "Symptom production on tobacco and tomato is determined by two distinct domains of the satellite RNA of cucumber mosaic virus (strain Y)." *J.Gen.Virol.* 70: 2765–2774.

Frisch, D. A., L. W. Harris-Haller, et al. (1995). "Complete Sequence of the binary vector Bin 19." *Plant Molecular Biology* 27: 405–409.

Guo, H. S. and J. A. Garcia (1997). "Delayed resistance to plum pox potyvirus mediated by a mutated RNA replicase gene: involvement of a gene-silencing mechanism." *Molecular Plant-Microbe Interactions* 10: 160–170.

Hamilton, W. D. O., M. Boccara, et al. (1987). "The complete nucleotide sequence of tobacco rattle virus RNA-1." *J.Gen.Virol.* 68: 2563–2375.

Hernandez, C., A. Mathis, et al. (1995). "Sequence of RNA 2 of a nematode transmissible isolate of tobacco rattle virus." *Journal Of General Virology* 76: 2847–2851.

Jones, L., A. J. Hamilton, et al. (1999). "RNA-DNA interactions and DNA methylation in post-transcriptional gene silencing." *Plant Cell* 11: 2291–2302.

Kjemtrup, S., K. S. Sampson, et al. (1998). "Gene silencing from plant DNA carried by a geminivirus." *Plant Journal* 14(1): 91–100.

Kumagai, M. H., J. Donson, et al. (1995). "Cytoplasmic inhibition of carotenoid biosynthesis with virus-derived RNA." *Proceedings Of The National Academy Of Sciences Of The United States Of America* 92: 1679–1683.

Lindbo, J. A., L. Silva-Rosales, et al. (1993). "Induction of a highly specific antiviral state in transgenic plants: implications for regulation of gene expression and virus resistance." *Plant Cell* 5: 1749–1759.

MacFarlane, S. A. (1999). "Molecular biology of the tobraviruses." *Journal Of General Virology* 80: 2799–2807.

Matthews, R. E. F. (1991). *Plant Virology*. San Diego, Calif., Academic Press.

Ratcliff, F., B. D. Harrison, et al. (1997). "A similarity between viral defense and gene silencing in plants." *Science* 276: 1558–1560.

Ratcliff, F., S. MacFarlane, et al. (1999). "Gene silencing without DNA: RNA-mediated cross protection between viruses." *Plant Cell* 11: 1207–1216.

Rodermel, S. R., M. S. Abbott, et al. (1988). "Nuclear-organelle interactions: Nuclear antisense gene inhibits ribulose bisphosphate carboxylase enzyme levels in transformed tobacco plants." *Cell* 55: 673–681.

Ruiz, M. T., O . Voinnet, et al. (1998). "Initiation and maintenance of virus-induced gene silencing." *Plant Cell* 10: 937–946.

Sambrook, J., E. F. Fritsch, et al. (1989). *Molecular Cloning: A Laboratory Manual.* New York, Cold Spring Harbor Laboratory Press.

Weigel, D., J. Alvarez, et al. (1992). "LEAFY Controls Floral Meristem Identity in Arabidopsis." *Cell* 69: 843–859.

Wilkinson, J. Q. and N. M. Crawford (1993). "Identification and characterisation of a chorate-resistant mutant of Arabidopsis thaliana with mutations in both nitrate reductase structural genes NIA1 and NIA2." *Molecular & General Genetics* 239: 289–297.

What is claimed is:

1. A nucleic acid vector which comprises:
   (a) a transfer nucleotide sequence comprising (i) a plant active promoter, operably linked to (ii) a recombinant tobacco rattle virus (TRV) cDNA which includes at least cis acting elements of TRV RNA2 permitting, in the presence of a replicase, replication of said cDNA as a cytoplasmically replicating RNA; a viral subgenomic promoter operably linked to a sequence encoding a TRV coat protein; and a heterologous nucleotide sequence which is foreign to said TRV virus; and
   (b) border sequences which permit the transfer of the transfer nucleotide sequence into a plant genome.

2. A vector as claimed in claim 1 wherein the plant promoter is the Cauliflower Mosaic Virus 35S gene promoter.

3. A vector as claimed in claim 1 wherein the border sequences are derived from *Agrobacterium tumefaciens*.

4. A vector as claimed in claim 1 wherein the replicase is not encoded by the vector.

5. A vector as claimed in claim 4 wherein non-essential open reading frames (ORFs) are deleted from the recombinant TRV cDNA.

6. A vector as claimed in claim 5 wherein the 37K and 32.8K ORFs are deleted from the recombinant TRV cDNA.

7. A process for gene silencing which comprises the of step introducing a vector as claimed in claim 4 into plant tissue, and optionally further includes the step of introducing one or more proteins encoded by TRV RNA1 into the plant tissue, wherein expression of said vector causes down-regulation of expression of said gene in said plant tissue.

8. A vector as claimed in claim 1 wherein the heterologous nucleotide sequence is a multiple cloning site.

9. A vector as claimed in claim 1 wherein the heterologous nucleotide sequence does not include, and is not operably linked to, a subgenomic promoter.

10. A vector as claimed in claim 1 wherein the heterologous nucleotide sequence is a targeting sequence which corresponds to a sequence in a target gene.

11. A vector as claimed in claim 10 wherein the target gene is a plant nuclear gene.

12. A vector as claimed in claim 10 wherein the targeting sequence which corresponds to a conserved sequence of a target gene.

13. A process for producing a vector as claimed in claim 10, which process comprises the step of cloning a heterologous nucleotide sequence which is a targeting sequence into a mutiple cloning site in the vector.

14. A method of silencing a target gene in a plant tissue using viral induced gene silencing (VIGS), which method comprises the step of introducing a vector claimed in claim 10 into the plant tissue, wherein the plant tissue is *Arabidopsis thaliana* or *Nicotiana benthamiian*, wherein expression of in said vector causes down-regulation of expression of said target gene.

15. A method as claimed in claim 14 for achieving substantially confluent VIGS of the target gene across a leaf.

16. A method as claimed in claim 14 for achieving VIGS of a target in meristematic tissue.

17. A method as claimed in claim 14 wherein the vector is introduced by Agrobacterium-mediated T-DNA transfer.

18. A method as claimed in claim 14 wherein the recombinant TRV cDNA in the vector is derived from TRV RNA2, and proteins encoded by TRV RNA1 are also introduced into the plant tissue.

19. A method as claimed in claim 18 wherein proteins encoded by TRV RNA1 are introduced by rub-inoculating the plant with purified TRV RNA1.

20. A method as claimed in claim 18 wherein proteins encoded by TRV RNA1 are introduced by transient Agrobacterium mediated expression in the plant of plasmid pBINTRA6.

21. A method as claimed in claim 14 wherein the plant tissue is *Arabidopsis thaliana*.

22. A method of characterising a target gene, which method comprises the steps of:
   a (a) silencing the target gene in a part, or at a certain development stage, of a plant using a method as claimed in claim 14,
   (b) observing the phenotype of the part of the plant in which or when the target gene has been silenced.

23. A method as claimed in claim 22 wherein the target gene is an essential gene.

24. A method of altering the phenotype of a plant comprising the step of silencing a target gene in the plant using a method as claimed in claim 14, wherein expression of said vector in said plant tissue silences said target gene thereby altering the phenotype of said plant.

25. A vector as claimed in claim 1 which is an expression vector.

26. A vector as claimed in claim 1 which is a viral induced gene silencing (VIGS) vector.

27. A method for gene silencing which comprises causing or allowing transcription from a vector as claimed in claim 1 in plant tissue such as to produce a cytoplasically-replicating RNA, wherein expression of said replicating RNA in said plant tissue causes down-regulation of expression of said gene.

28. A virus or viral particle which comprises an encapsulated RNA transcript from a vector as claimed in claim 1.

29. A kit comprising a vector as claimed in claim 1 further including at least one of a source of TRV RNA1 polypeptide or a vector encoding said polypeptide.

30. A host cell comprising a vector as claimed in claim 1.

31. Plant tissue comprising or transiently transformed by a vector as claimed in claim 1.

32. A vector which is pTV00, SEQ ID NO: 37.

* * * * *

UNITED STATES PATENT AND TRADEMARK OFFICE
CERTIFICATE OF CORRECTION

PATENT NO.    : 6,369,296 B1
DATED         : April 9, 2002
INVENTOR(S)   : Frank Giles Ratcliff et al.

It is certified that error appears in the above-identified patent and that said Letters Patent is hereby corrected as shown below:

Column 8,
Line 20, insert -- (SEQ ID No: 37) -- before the period;
Line 21, insert -- (SEQ ID No: 38) -- before the period;
Line 22, insert -- (SEQ ID No: 39) -- before the period;
Line 23, insert -- (SEQ ID No: 40) -- before the period;
Line 24, insert -- (SEQ ID No: 41) -- before the period;
Line 25, insert -- (SEQ ID No: 42) -- before the period;
Line 26, insert -- (SEQ ID No: 43) -- before the period;
Line 27, insert -- partial -- in place of "full" and insert -- (SEQ ID No: 44) -- before the period.

Column 11,
Line 3, replace "full" with -- partial --.

Columns 17 and 18,
Line 1, "Key to sequence annotation", please replace "Complete" with
-- Partial --
Line 37, insert -- Key to sequence annotation -- (a total of 12 pages) as shown on attached pages.

Column 48,
Delete claim 20.

Signed and Sealed this

Twenty-sixth Day of November, 2002

Attest:

Attesting Officer

JAMES E. ROGAN
Director of the United States Patent and Trademark Office

Key to sequence annotation:

| | |
|---|---|
| Lower-case | plasmid backbone sequence |
| *Lower-case italics* | sequence inserted to the pTV00 or pGR107 vectors |
| Lower-case underlined | CaMV 35S promoter sequence |
| UPPER-CASE | tobravirus cDNA sequence |
| *UPPER-CASE ITALICS* | Nopaline synthase terminator sequence |
| UPPER-CASE AND BOLD | Arabidopsis NIA1-intron 3 sequence |
| Lower-case and bold | CaMV35S terminator sequence |

1: pTV00 sequence.

tttttatccccggaagcctgtggatagagggtagttatccacgtgaaaccgctaatgccccgcaaagccttgattcacggggcttt
ccggcccgctccaaaaactatccacgtgaaatcgctaatcagggtacgtgaaatcgctaatcggagtacgtgaaatcgctaata
aggtcacgtgaaatcgctaatcaaaaaggcacgtgagaacgctaatagcccttcagatcaacagcttgcaaacacccctcgct
ccggcaagtagttacagcaagtagtatgttcaattagcttttcaattatgaatatatatatcaattattggtcgcccttggcttgtgga
caatgcgctacgcgcaccggctccgcccgtggacaaccgcaagcggttgcccaccgtcgagcgccagcgcctttgcccaca
acccggcggccggccgcaacagatcgttttataaatttttttttttgaaaaagaaaaagcccgaaaggcggcaacctctcgggct
tctggatttccgatccccggaattagatctcaaacaaacacatacagcgacttagtttacccgccaatatatcctgtcaaggccttc
atgttctttcctgcgttatcccctgattctgtggataaccgtattaccgcctttgagtgagctgataccgctcgccgcagccgaacg
accgagcgcagcgagtcagtgagcgaggaagcggaagagcgcccaatacgcaaaccgcctctccccgcgcgttggccga
ttcattaatgcagctggcacgacaggtttcccgactggaaagcgggcagtgagcgcaacgcaattaatgtgagttagctcactc
attaggcaccccaggctttacactttatgcttccggctcgtatgttgtgtggaattgtgagcggataacaatttcacacaggaaaca
gctatgaccatgattacgccaagctcggaattaaccctcactaaagggaacaaaagctggagctcc<u>accgcggtggagctcc</u>
<u>accggggaaacctcctcgggattccattgcccagctatctgtcactttattgagaagatagtggaaaaggaaggtggctcctac</u>
<u>aaatgccatcattgcgataaaggaaaggccatcgttgaagatgcctctgccgacagtggtcccaaagatggaccccacccac</u>
<u>gaggagcatcgtggaaaaagaagacgttccaaccacgtcttcaaagcaagtggattgatgtgatatctccactgacgtaaggg</u>
<u>atgacgcacaatcccactatccttcgcaagacccttcctctatataaggaagttcatttcatttggagaggctag</u>ATAAAAC

2

ATTGCACCTATGGTGTTGCCCTGGCTGGGGTATGTCAGTGATCGCAGTAGAA
TGTACTAATTGACAAGTTGGAGAATACGGTAGAACGTCCTTATCCAACACAG
CCTTTATCCCTCTCCCTGACGAGGTTTTGTCAGTGTAATATTTCTTTTTGAAC
TATCCAGCTTAGTACCGTACGGGAAAGTGACTGGTGTGCTTATCTTTGAAAT
GTTACTTTGGGTTTCGGTTCTTTAGGTTAGTAAGAAAGCACTTGTCTTCTCAT
ACAAAGGAAAACCTGACGTATCGCTTACGAAAGTAGCAATGAAAGAAGGT
GGTGGTTTTAATCGTACCGCAAAAACGATGGGGTCGTTTTAATTAACTTCT
CCTACAAGCGTCTAAACGGACGTTGGGGTTTTGCTAGTTTCTTTAGAGAAAA
CTAGCTAAGTCTTTAATGTTATCATTAGAGATGGCATAAATATAATACTTGT
GTCTGCTGATAAGATCATTTTAATTTGGACGATTAGACTTGTTGAACTACAG
GTTACTGAATCACTTGCGCTAATCAACATGGGAGATATGTACGATGAATCAT
TTGACAAGTCGGGCGGTCCTGCTGACTTGATGGACGATTCTTGGGTGGAATC
AGTTTCGTGGAAAGATTTGTTGAAGAAGTTACACAGCATAAAATTTGCACTA
CAGTCTGGTAGAGATGAGATCACTGGGTTACTAGCGGCACTGAATAGACAG
TGTCCTTATTCACCATATGAGCAGTTTCCAGATAAGAAGGTGTATTTCCTTTT
AGACTCACGGGCTAACAGTGCTCTTGGTGTGATTCAGAACGCTTCAGCGTTC
AAGAGACGAGCTGATGAGAAGAATGCAGTGGCGGGTGTTACAAATATTCCT
GCGAATCCAAACACAACGGTTACGACGAACCAAGGGAGTACTACTACTACC
AAGGCGAACACTGGCTCGACTTTGGAAGAAGACTTGTACACTTATTACAAAT
TCGATGATGCCTCTACAGCTTTCCACAAATCTCTAACTTCGTTAGAGAACAT
GGAGTTGAAGAGTTATTACCGAAGGAACTTTGAGAAAGTATTCGGGATTAA
GTTTGGTGGAGCAGCTGCTAGTTCATCTGCACCGCCTCCAGCGAGTGGAGGT
CCGATACGTCCTAATCCCTAGGGATTTAAGGACGTGAACTCTGTTGAGATCC
TAGAactagtggatccccgggctgcaggaattcgatatcaagcttatcgataccgtcgacctcgagggggggcccggta
cccAATTCGCCCTATAGTGAGTCGTATTACAATTCACTGGCCGTCGTTTTACAA
CGTCGTGACTGGGAAAACCCTGGCGTTACCCAACTTAATCGCCTTGCAGCAC
ATCCCCCTTTCGCCAGCTGGCGTAATAGCGAAGAGGCCCGCACCGATCGCCC

3

TTCCCAACAGTTGCGAAGACATTAAACTACGGTTCTTTAAGTAGATCCGTGC
CTGAAGTTTTAGGTTCAATTTAAACCTACGAGATTGACATTCTCGACTGATCT
TGATTGATCGGTAAGTCTTTTGTAATTTAATTTTCTTTTTGATTTTATTTTAAA
TTGTTATCTGTTTCTGTGTATAGACTGTTTGAGATCGGCGTTTGGCCGACTCA
TTGTCTTACCATAGGGGAACGGACTTTGTTTGTGTTGTTATTTTATTTGTATTT
TATTAAAATTCTCAACGATCTGAAAAAGCCTCGCGGCTAAGAGATTGTTGGG
GGGTGAGTAAGTACTTTTAAAGTGATGATGGTTACAAAGGCAAAAGGGGTA
AAACCCCTCGCCTACGTAAGCGTTATTACGCCCTCGAGTATCGAATTGCTGC
AGGCATGCAAGCGATCCCCGATCGTTCAAACATTTGGCAATAAAGTTTCTTA
AGATTGAATCCTGTTGCCGGTCTTGCGATGATTATCATATAATTTCTGTTGAA
TTACGTTAAGCATGTAATAATTAACATGTAATGCAT*GACGTTATTTATGAGATG*
*GGTTTTTATGATTAGAGTCCCGCAATTATACATTTAATACGCGATAGAAAACAAAAT*
*ATAGCGCGCAAACTAGGATAAATTATCGCGCGGTGTCATCTATGTTACTAGATC*
*GGGAATTGCCAAGCTGCTTGGCACTGGCCGTCGTTTTACAACGTCGTGACTGGGA*
*AAACCCTGGCGTTACCCAACTTAATCGCCTTGCAGCACATCCCCCTTTCGCCAGC*
*TGGCGTAATAGCGAAGAGGCCCGCACCGATCGCCCTTCCCAACAGTTGCGCA*gcct
gaatggcgaatggcgcgaaattgtaaacgttaatgttaacgttacaccacaatatatcctgccaagatctcatgtgagcaaaagg
ccagcaaaaggccaggaaccgtaaaaaggccgcgttgctggcgttttccataggctccgcccccctgacgagcatcacaaa
aatcgacgctcaagtcagaggtggcgaaacccgacaggactataaagataccaggcgtttccccctggaagctccctcgtgc
gctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgcct
tatccggtaactatcgtcttgagtccaacccggtaagacacgacttatcgccactggcagcagccactggtaacaggattagca
gagcgaggtatgtaggcggtgctacagagttcttgaagtggtggcctaactacggctacactagaaggacagtatttggtatct
gcgctctgctgaagccagttaccttcggaaaaagagttggtagctcttgatccggcaaacaaaccaccgctggtagcggtggtt
tttttgtttgcaagcagcagattacgcgcagaaaaaaaggatctcaagaagatcctttgatcttttctacggggtctgacgctcagt
ggaacgaaaactcacgttaagggattttggtcatggttacaaccaattaaccaattctgattagaaaaactcatcgagcatcaaat
gaaactgcaatttattcatatcaggattatcaataccatattttgaaaaagccgtttctgtaatgaaggagaaaactcaccgaggc agttccataggatggcaagatcctggtatcggtctgcgattccgactcgtccaacatcaatacaacctattaatttcccctcgtcaa
aaataaggttatcaagtgagaaatcaccatgagtgacgactgaatccggtgagaatggcaaaagtttatgcatttctttccagact
tgttcaacaggccagccattacgctcgtcatcaaaatcactcgcatcaaccaaaccgttattcattcgtgattgcgcctgagcgag
acgaaatacgcgatcgctgttaaaaggacaattacaaacaggaatcgaatgcaaccggcgcaggaacactgccagcgcatc
aacaatattttcacctgaatcaggatattcttctaatacctggaatgctgttttccctgggatcgcagtggtgagtaaccatgcatca
tcaggagtacggataaaatgcttgatggtcggaagaggcataaattccgtcagccagtttagtctgaccatctcatctgtaacatc
attggcaacgctacctttgccatgtttcagaaacaactctggcgcatcgggcttcccatacaatccatagattgtcgcacctgattg
cccgacattatcgcgagcccatttatacccatataaatcagcatccatgttggaatttaatcgcggcctggagcaagacgtttccc
gttgaatatggctcataacaccccttgtattactgtttatgtaagcagacagttttattgttcatgatgatatattttatcttgtgcaatgt
aacatcagagattttgagacacaacgtggctttgttgaataaatcgaacttttgctgagttgaaggatcagatcacgcatcttcccg
acaacgcagaccgttccgtggcaaagcaaaagttcaaaatcaccaactggtccacctacaacaaagctctcatcaaccgtgct
ccctcactttctggctggatgatggggcgattcaggcgatccccatccaacagcccgccgtcgagcgggct

(2) PEBV coat protein promoter:

GGATCCGCACACAAGGTTAAAAACGCTGTAGTAATACATGCGCAAGAACAG
GCTGAGCATCTTGTTCTGGGGTTTCACACTATCTTTAGAGAAAGTGTTAAGTT
AATTAAGTTATCTTAATTAAGAGCATAATTATACTGATTTGTCTCTCGTTGAT
AGAGTCTATCATTCTGTTCTAAAAATTTGACAACTCGGTTTGCTGACCTACTG
GTTACTGTATCACTTACCCGAGTTAACGAGGGCGCGCCC

(3) *N. benthamiana* pds partial cDNA sequence:

*tctgtcaaaccatatatggacatttatcacaggaactcccactagcttctccaacttttggaaatatgggatctctttccagtctt*
*caggcaaaagaagcttcaagatatccactggagtggcaaacacaaaagcatctcctttaattgtactgccattattctgtata*
*aaacatttgacacttccatcctcattcagctcgatctttttattcgtgagtttagtctgacttggccacctttgactcaatatgttc* cacaatcggcatgcaaagtctctcaggagggttaccatctaaaaaggccattttttgaaccatgtttctcctgaagaaatctgtt
caaagcaatcaagatgcactgcatcgaaagctcgtcagggtttataaagttgagtgcctctagactg

(4) *A. thaliana* pds partial cDNA sequence:

ctcgagagatgtcaaatctgtgagattcatttactgaagagagtaaggttaagtttggattgcaatgagatttatacacaaat
aataatgcttacaagcaaatcatctttaagttttgtcctcttctcatgatgatgatactgttgcctccgacaactttcttggtccag
acgcagccagtagctcgtaatcctgaacaatagactgagagcagaatttgccagagaggacagcgccttccatggaagc
taagtacttctgttttgtgtaatctccagctaagtagaatccttcaataggtgatctttgtagaggacgacatggttcacagtttg
ggatggtcttgtacacagatcttggagtcttaacgacatggtacttcagaatttagctttgctttggtcagctgagatttcatca
gggaagagtttctcaagttctttcattgttgcatctatgatgtcagaatcagtccgtgatatccattcctctgctggtgcaaatact
agctccagcattgaccggttaggatcgtaatattccttacaagttaaggacatgtcggcatacacgctcagaaggttacttct
gctaaagagtaggtgatcatatgtgttcttcagttttcgatcaaaccatatatgaacattaataactggtactccaactaatttat
ccaatttcttgaagtacggtatttctttccagggatctggtaaaaggagcttcaggatatcgactggagcggcaaacacata
agcgtctccttcgacagtgcttccattagtgagtaagaaactcttaaccgtgccatcgtcattgagctcaatttctttatcctag
aattaagttgcacttccccacctagtgatcgaatatgatccactactggcatacaaagcctttccggaggattaccatccaag
aatgccatcttggaaccatgtttttcctgaagaaaccggttcaaagctatcaaaatgcattgcattgacagttcatcagggttt
ataaagtttagcgcctttgacatggcaataaacacctcgtcggtcacgcgctcaggtactccctgcttttccatccattctttga
ctgataaaccatcttgggcctcaacataagcctgaccgccgaccatggctggcaaaagtccaatagcaaactttattttctct
ggccatgtcagcatctcgttgttccgcaaaatagcccaaataccatttaagggtgctggtaggacatctgggaagtcaaatc
tactaaattctccaggtttacttggcatagcaaaaatcatggagtgttccttccactgcaaccgatcattgatcccaagttctcc
aaataaattctgcacattcggataagcaccgaagaaaatatgtaaaccagtctcataccagtccccatcttcatccttccatg
cagctatctttccaccaagaacatctcttgcttcaagcaacagaggtttgtggcctgcatcagccaggtactttgcagttgaca
atccagccaatccagcaccagcaattacaactttcaaaggcttagcaggacgaggagcactacggaaggatgcagata
aactagcagcttccaagaaattgacagtgttctctagctctggccttggaatatccacacaaactacctgcaaaggaccag
cagtactcctcctccttgttcttgtcttaagcgcttgagaagtgggaaccctaaagctatgtcccattagttcacaacctccaga
tgaaagtgcctcgag

(5) *N. benthamiana* rubisco partial cDNA sequence;

*agtctagatggcttcctcagttctttcctctgcagcagttgccacccgcagcaatgttgctcaagctaacatggttgcacctttc actggccttaagtcagctgcctcattccctgtttcaaggaagcaaaaccttgacatcacttccattgccagcaacggcggaa gagtgcaatgcatgcaggtgtggccaccaattaacaagaagaagtacgagactctctcataccttcctgatttgagccagg agcaattgcttagtgaagttgagtaccttttgaaaaatggatgggttccttgcttggaattcgagactgagcacggatttgtcta ccgtgaaaacaacaagtcaccaggatactatgatggcagatactggaccatgtggaagctacctatttcggatgcactgat gccacccaagtgttggctgaggtggaagaggcgaagaaggcatacccacaggcctggatccgtatcattggattcgaca acgtgg*

(6) Partial cDNA sequence from the 3' end of GFP

*gatggaaacattcttggacacaaattggaatacaactataactcacacaatgtatacatcatggcagacaaacaaaagaa tggaatcaaagttaacttcaaaattagacacaacattgaagatggaagcgttcaactagcagaccattatcaacaaata ctccaattggcgatggccctgtcctttaccagacaaccattacctgtccacacaatctgcccttttcgaaagatcccaacgaa aagagagaccacatggtccttcttgagtttgtaacagctgctgggattacacatggcatggatgaactatacaaataa*

(7) *N. benthamiana* partial cDNA sequence from NFL

*tggacccagaggctttctcagcgagtttgttcaaatgggaccctagaggtgcaatgccaccgccaacccggctgttggaag ccgcggtggcgcctcctcctccaccaccagttctgccaccgccgcagcctctatcggcggcctattccattaggacaaggg agttaggagggctagaggagttgtttcaagcttacggtatacgttattacactgctgctaaaatagcggagctaggttttacg gtgaatactctattggacatgaaagatgaggaacttgatgatatgatgaatagcctttcacagattttcagatgggaactcct cgtcggagaaaggtacggtatcaaagctgcaatcagggcggaacggcggaggcttgaggaggaagaactacggcgg cgcagccaccttctgtc*

(8) Partial sequence of Pbintra 6 plasmid.

tactccaaaaatgtcaaagatacagtctcagaagaccaaagggctattgagacttttcaacaaagggtaatttcgggaaacctcc
tcggattccattgcccagctatctgtcacttcatcgaaaggacagtagaaaaggaaggtggctcctacaaatgccatcattgcga
taaaggaaaggctatcattcaagatgcctctgccgacagtggtcccaaagatggaccccacccacgaggagcatcgtggaa
aaagaagacgtcccaaccacgtcttcaaagcaagtggattgatgtgacatctccactgacgtaagggatgacgcacaatccca
ctatccttcgcaagacccttcttctatataaggaagttcatttcatttggagaggacagcccaagctttctagagGATCCAT
AAAACATTTCAATCCTTTGAACGCGGTAGAACGTGCTAATTGGATTTTGGTG
AGAACGCGGTAGAACGTACTTATCACCTACAGTTTTATTTTGTTTTTCTTTTT
GGTTTAATCTATCCAGCTTAGTACCGAGTGGGGGAAAGTGACTGGTGTGCCT
AAAACCTTTTCTTTGATACTTTGTAAAAATACATACAGATACAATGGCGAAC
GGTAACTTCAAGTTGTCTCAATTGCTCAATGTGGACGAGATGTCTGCTGAGC
AGAGGAGTCATTTCTTTGACTTGATGCTGACTAAACCTGATTGTGAGATCGG
GCAAATGATGCAAAGAGTTGTTGTTGATAAAGTCGATGACATGATTAGAGA
AAGAAAGACTAAAGATCCAGTGATTGTTCATGAAGTTCTTTCTCAGAAGGAA
CAGAACAAGTTGATGGAAATTTATCCTGAATTCAATATCGTGTTTAAAGACG
ACAAAAACATGGTTCATGGGTTTGCGGCTGCTGAGCGAAAACTACAAGCTTT
ATTGCTTTTAGATAGAGTTCCTGCTCTGCAAGAGGTGGATGACATCGGTGGT
CAATGGTCGTTTTGGGTAACTAGAGGTGAGAAAAGGATTCATTCCTGTTGTC
CAAATCTAGATATTCGGGATGATCAGAGAGAAATTTCTCGACAGATATTTCT
TACTGCTATTGGTGATCAAGCTAGAAGTGGTAAGAGACAGATGTCGGAGAA
TGAGCTGTGGATGTATGACCAATTTCGTGAAAATATTGCTGCGCCTAACGCG
GTTAGGTGCAATAATACATATCAGGGTTGTACATGTAGGGGTTTTTCTGATG
GTAAGAAGAAAGGCGCGCAGTATGCGATAGCTCTTCACAGCCTGTATGACTT
CAAGTTGAAAGACTTGATGGCTACTATGGTTGAGAAGAAAACTAAAGTGGT
TCATGCTGCTATGCTTTTTGCTCCTGAAAGTATGTTAGTGGACGAAGGTCCAT
TACCTTCTGTTGACGGTTACTACATGAAGAAGAACGGGAAGATCTATTTCGG
TTTTGAGAAAGATCCTTCCTTTTCTTACATTCATGACTGGGAAGAGTACAAG

8

AAGTATCTACTGGGGAAGCCAGTGAGTTACCAAGGGAATGTGTTCTACTTCG
AACCGTGGCAGGTGAGAGGAGACACAATGCTTTTTCGATCTACAGGATAG
CTGGAGTTCCGAGGAGGTCTCTATCATCGCAAGAGTACTACCGAAGAATATA
TATCAGTAGATGGGAAAGCATGGTTGTTGTCCCAATTTTCGATCTGGTCGAA
TCAACGCGAGAGTTGGTCAAGAAAGACCTGTTTGTAGAGAAACAATTCATG
GACAAGTGTTTGGATTACATAGCTAGGTTATCTGACCAGCAGCTGACCATAA
GCAATGTTAAATCATACTTGAGTTCAAATAATTGGGTCTTATTCATAAACGG
GGCGGCCGTGAAGAACAAGCAAAGTGTAGATTCTCGAGATTTACAGTTGTT
GGCTCAAACTTTGCTAGTGAAGGAACAAGTGGCGAGACCTGTCATGAGGGA
GTTGCGTGAAGCAATTCTGACTGAGACGAAACCTATCACGTCATTGACTGAT
GTGCTGGGTTTAATATCAAGAAAACTGTGGAAGCAGTTTGCTAACAAGATCG
CAGTCGGCGGATTCGTTGGCATGGTTGGTACTCTAATTGGATTCTATCCAAA
GAAGGTACTAACCTGGGCGAAGGACACACCAAATGGTCCAGAACTATGTTA
CGAGAACTCGCACAAAACCAAGGTGATAGTATTTCTGAGTGTTGTGTATGCC
ATTGGAGGAATCACGCTTATGCGTCGAGACATCCGAGATGGACTGGTGAAA
AAACTATGTGATATGTTTGATATCAAACGGGGGGCCCATGTCTTAGACGTTG
AGAATCCGTGCCGCTATTATGAAATCAACGATTTCTTTAGCAGTCTGTATTC
GGCATCTGAGTCCGGTGAGACCGTTTTACCAGATTTATCCGAGGTAAAAGCC
AAGTCTGATAAGCTATTGCAGCAGAAGAAAGAAATCGCTGACGAGTTTCTA
AGTGCAAAATTCTCTAACTATTCTGGCAGTTCGGTGAGAACTTCTCCACCAT
CGGTGGTCGGTTCATCTCGAAGCGGACTGGGTCTGTTGTTGGAAGACAGTAA
CGTGCTGACCCAAGCTAGAGTTGGAGTTTCAAGAAAGGTAGACGATGAGGA
GATCATGGAGCAGTTTCTGAGTGGTCTTATTGACACTGAAGCAGAAATTGAC
GAGGTTGTTTCAGCCTTTTCAGCTGAATGTGAAAGAGGGGAAACAAGCGGT
ACAAAGGTGTTGTGTAAACCTTTAACGCCACCAGGATTTGAGAACGTGTTGC
CAGCTGTCAAACCTTTGGTCAGCAAAGGAAAAACGGTCAAACGTGTCGATT
ACTTCCAAGTGATGGGAGGTGAGAGATTACCAAAAAGGCCGGTTGTCAGTG

GAGACGATTCTGTGGACGCTAGAAGAGAGTTTCTGTACTACTTAGATGCGGA
GAGAGTCGCTCAAAATGATGAAATTATGTCTCTGTATCGTGACTATTCGAGA
GGAGTTATTCGAACTGGAGGTCAGAATTACCCGCACGGACTGGGAGTGTGG
GATGTGGAGATGAAGAACTGGTGCATACGTCCAGTGGTCACTGAACATGCTT
ATGTGTTCCAACCAGACAAACGTATGGATGATTGGTCGGGATACTTAGAAGT
GGCTGTTTGGGAACGAGGTATGTTGGTCAACGACTTCGCGGTCGAAAGGAT
GAGTGATTATGTCATAGTTTGCGATCAGACGTATCTTTGCAATAACAGGTAA
TAATCCTCTCTCTTGATATTTTAAATTATAGAATTAATTAGTTTACTTTA
TTCTTTACTATATGATTTAAATAGTTTAATCTTGTTTTTGAGTAAACTAT
TCGATTTTGATATTTGTATTCGTCCTACAAAGTTGGAAATACTGATGATA
TTTTCTTTTGAACGTGATACCTACCAATACTAATCTTACGGAATCTTTTA
ATAGAGCACTAATCAACATGGAACTAAAGACCAATTCTTAAGTGTCTCT
GTTGTACAGTTCATTTTAGTAGTGCGTTTAAGTATTATTATCTCCCTTCA
TGCGGGGCAATTATGTAGATTAAAATCGAATTATATAAAATTTACATA
AGTCTAAGTCTAGGGTCTCCAGCTAATTGTTATTTTTTAACGATGTTGA
CTAAAGCAATAACGACGTTGACTTGTGTTAAACAGGTTGATCTTGGACAA
TTTAAGTGCCCTGGATCTAGGACCAGTTAACTGTTCTTTTGAATTAGTTGACG
GTGTACCTGGTTGTGGTAAGTCGACAATGATTGTCAACTCAGCTAATCCTTG
TGTCGATGTGGTTCTCTCTACTGGGAGAGCAGCAACCGACGACTTGATCGAG
AGATTCGCGAGCAAAGGTTTTCCATGCAAATTGAAAAGGAGAGTGAAGACG
GTTGATTCTTTTTGATGCATTGTGTCGATGGTTCTTTAACCGGAGACGTGTT
GCATTTCGACGAAGCTCTCATGGCCCATGCTGGTATGGTGTACTTTGCGCTC
AGATAGCTGGTGCTAAACGATGTATCTGTCAAGGAGATCAGAATCAAATTTC
TTTCAAGCCTAGGGTATCTCAAGTTGATTTGAGGTTTTCTAGTCTGGTCGGAA
AGTTTGACATTGTTACAGAAAAAGAGAAACTTACAGAAGTCCAGCAGATG
TGGCTGCCGTATTGAACAAGTACTATACTGGAGATGTCAGAACACATAACGC
GACTGCTAATTCGATGACGGTGAGGAAGATTGTGTCTAAAGAACAGGTTTCT

10

TTGAAGCCTGGTGCTCAGTACATAACTTTCCTTCAGTCTGAGAAGAAGGAGT
TGGTAAATTTGTTGGCATTGAGGAAAGTGGCAGCTAAAGTGAGTACAGTAC
ACGAGTCGCAAGGAGAGACATTCAAAGATGTAGTCCTAGTCAGGACGAAAC
CTACGGATGACTCAATCGCTAGAGGTCGGGAGTACTTAATCGTGGCATTGTC
GCGTCACACACAATCACTTGTGTATGAAACTGTGAAAGAGGACGATGTAAG
CAAAGAGATCAGGGAAAGTGCCGCGCTTACGAAGGCGGCTTTGGCAAGATT
TTTGTTACTGAGACCGTCTTATGACGGTTTCGGTCTAGGTTTGATGTCTTTA
GACATCATGAAGGGCCTTGCGCCGTTCCAGATTCAGGTACGATTACGGACTT
GGAGATGTGGTACGACGCTTTGTTTCCGGGAAATTCGTTAAGAGACTCAAGC
CTAGACGGGTATTTGGTGGCAACGACTGATTGCAATTTGCGATTAGACAATG
TTACGATCAAAAGTGGAAACTGGAAAGACAAGTTTGCTGAAAAGAAACGT
TTCTGAAACCGGTTATTCGTACTGCTATGCCTGACAAAGGAAGACTACTCA
GTTGGAGAGTTTGTTAGCATTGCAGAAAAGGAACCAAGCGGCACCCGATCT
ACAAGAAAATGTGCACGCGACAGTTCTAATCGAAGAGACGATGAAGAAGCT
GAAATCTGTTGTCTACGATGTGGGAAAAATTCGGGCTGATCCTATTGTCAAT
AGAGCTCAAATGGAGAGATGGTGGAGAAATCAAAGCACAGCGGTACAGGCT
AAGGTAGTAGCAGATGTGAGAGAGTTACATGAAATAGACTATTCGTCTTAC
ATGTATATGATCAAATCTGACGTGAAACCTAAGACTGATTTAACACCGCAAT
TTGAATACTCAGCTCTACAGACTGTTGTGTATCACGAGAAGTTGATCAACTC
GTTGTTCGGTCCAATTTTCAAAGAAATTAATGAACGCAAGTTGGATGCTATG
CAACCACATTTTGTGTTCAACACGAGAATGACATCGAGTGATTTAAACGATC
GAGTGAAGTTCTTAAATACGGAAGCGGCTTACGACTTTGTTGAGATAGACAT
GTCTAAATTCGACAAGTCGGCAAATCGCTTCCATTTACAACTGCAGCTGGAG
ATTTACAGGTTATTTGGGCTGGATGAGTGGGCGGCCTTCCTTTGGGAGGTGT
CGCACACTCAAACTACTGTGAGAGATATTCAAAATGGTATGATGGCGCATAT
TTGGTACCAACAAAGAGTGGAGATGCTGATACTTATAATGCAAATTCAGAT
AGAACACTGTGTGCACTCTTGTCTGAATTACCATTGGAGAAAGCAGTCATGG

TTACATATGGAGGAGATGACTCACTGATTGCGTTTCCTAGAGGAACGCAGTT
TGTTGATCCGTGTCCAAAGTTGGCTACTAAGTGGAATTTCGAGTGCAAGATT
TTTAAGTACGATGTCCCAATGTTTTGTGGGAAGTTCTTGCTTAAGACGTCATC
GTGTTACGAGTTCGTGCCAGATCCGGTAAAAGTTCTGACGAAGTTGGGGAA
AAAGAGTATAAAGGATGTGCAACATTTAGCCGAGATCTACATCTCGCTGAAT
GATTCCAATAGAGCTCTTGGGAACTACATGGTGGTATCCAAACTGTCCGAGT
CTGTTTCAGACCGGTATTTGTACAAAGGTGATTCTGTTCATGCGCTTTGTGCG
CTATGGAAGCATATTAAGAGTTTTACAGCTCTGTGTACATTATTCCGAGACG
AAAACGATAAGGAATTGAACCCGGCTAAGGTTGATTGGAAGAAGGCACAGA
GAGCTGTGTCAAACTTTTACGACTGGTAATATGGAAGACAAGTCATTGGTCA
CCTTGAAGAAGAAGACTTTCGAAGTCTCAAAATTCTCAAATCTAGGGGCCAT
TGAATTGTTTGTGGACGGTAGGAGGAAGAGACCGAAGTATTTTCACAGAAG
AAGAGAAACTGTCCTAAATCATGTTGGTGGGAAGAAGAGTGAACACAAGTT
AGACGTTTTTGACCAAAGGGATTACAAAATGATTAAATCTTACGCGTTTCTA
AAGGTAGTAGGTGTACAACTAGTTGTAACATCACATCTACCTGCAGATACGC
CTGGGTTCATTCAAATCGATCTGTTGGATTCGAGACTTACTGAGAAAAGAAA
GAGAGGAAAGACTATTCAGAGATTCAAAGCTCGAGCTTGCGATAACTGTTC
AGTTGCGCAGTACAAGGTTGAATACAGTATTTCCACACAGGAGAACGTACTT
GATGTCTGGAAGGTGGGTTGTATTTCTGAGGGCGTTCCGGTCTGTGACGGTA
CATACCCTTTCAGTATCGAAGTGTCGCTAATATGGGTTGCTACTGATTCGACT
AGGCGCCTCAATGTGGAAGAACTGAACAGTTCGGATTACATTGAAGGCGAT
TTTACCGATCAAGAGGTTTTCGGTGAGTTCATGTCTTTGAAACAAGTGGAGA
TGAAGACGATTGAGGCGAAGTACGATGGTCCTTACAGACCAGCTACTACTA
GACCTAAGTCATTATTGTCAAGTGAAGATGTTAAGAGAGCGTCTAATAAGA
AAAACTCGTCTTAATGCATAAAGAAATTTATTGTCAATATGACGTGTGTACT
CAAGGGTTGTGTGAATGAAGTCACTGTTCTTGGTCACGAGACGTGTAGTATC
GGTCATGCTAACAAATTGCGAAAGCAAGTTGCTGACATGGTTGGTGTCACAC

GTAGGTGTGCGGAAAATAATTGTGGATGGTTTGTCTGTGTTGTTATCAATGA
TTTTACTTTTGATGTGTATAATTGTTGTGGCCGTAGTCACCTTGAAAAGTGTC
GTAAACGTGTTGAAACAAGAAATCGAGAAATTTGGAAACAAATTCGACGAA
ATCAAGCTGAAAACATGTCTGCGACAGCTAAAAAGTCTCATAATTCGAAGA
CCTCTAAGAAGAAATTCAAAGAGGACAGAGAATTTGGGACACCAAAAAGAT
TTTTAAGAGATGATGTTCCTTTCGGGATTGATCGTTTGTTTGCTTTTTGATTTT
ATTTTATATTGTTATCTGTTTCTGTGTATAGACTGTTTGAGATTGGCGCTTGG
CCGACTCATTGTCTTACCATAGGGGAACGGACTTTGTTTGTGTTGTTATTTTA
TTTGTATTTTATTAAAATTCTCAATGATCTGAAAAGGCCTCGAGGCTAAGAG
ATTATTGGGGGGTGAGTAAGTACTTTTAAAGTGATGATGGTTACAAAGGCAA
AAGGGGTAAAACCCCTCGCCTACGTAAGCGTTATTACGCCCgatccccgggagc
tcgaattcgctgaaatcaccagtctctctctacaaatctatctctctcttatttttttccataaataatgtgtgagtagtttcccgataa
gggaaattagggttcttataggttttcgctcatgtgttgagcatataagaaacccttagtatgtatttgtatttgtaaaata
cttctattatcaataaaatttctaattcctaaaaccaaaatccagtactaaaatccagatctcctaaagtccctatagatct
ttgtcgtgaatataaaccagacacgagacgactaaacctggagcccagacgccgttcgaagctagaagtaccgcttag
gcaggaggccgttagggaaaagatgctaaggcagggttggttacgttgactcccccgtaggtttggtttaaatatgatg
aagtggacggaaggaaggaggaagacaaggaaggataaggttgcaggccctgtgcaaggtaagaagatggaaatt
tgatagaggtacgctactatacttatactatacgctaagggaatgcttgtatttatacctatacccctaataacccctta
tcaatttaagaaataatccgcataagcccccgcttaaaaattggtatcagagccatgaataggtctatgaccaaaactc
aagaggataaaacctcaccaaaatacgaaagagttcttaactctaaagataaaagatctttcaagatcaaaactagtt
ccctcacaccggagcatgcgatatcctcgacctgcaggcatgcaagcttggcgtaatcatggtcatagctgtttcctgtgtgaaa
ttgttatccgctcacaattccacacaacatacgagccggaagcataaagtgtaaagcctggggtgcctaatgagtgagctaact
cacattaattgcgttgcgctcactgcccgctttccagtcgggaaacctgtcgtgccagctgcattaatgaatcggccaacgcgcg
gggagaggcggtttgcgtattgggccaaagacaaaagggcgacattcaaccgattgagggagggaaggtaaatattgacgg
aaattattcattaaaggtgaattatcaccgtcaccgacttgagccatttgggaattagagccagcaaaatcaccagtagcaccatt
accattagcaaggccggaaacgtcaccaatgaaaccatcgatagcagcaccgtaatcagtagcgacagaatcaagtttgcctttt
agcgtcagactgtagcgcgttttcatcggcattttcggtcatagcccccttattagcgtttgccatcttttcataatcaaaatcaccg

UNITED STATES PATENT AND TRADEMARK OFFICE
CERTIFICATE OF CORRECTION

PATENT NO.    : 6,369,296 B1
DATED         : April 9, 2002
INVENTOR(S)   : Frank Giles Ratcliff et al.

It is certified that error appears in the above-identified patent and that said Letters Patent is hereby corrected as shown below:

Column 8,
Line 20, insert -- (SEQ ID No: 37) -- before the period;
Line 21, insert -- (SEQ ID No: 38) -- before the period;
Line 22, insert -- (SEQ ID No: 39) -- before the period;
Line 23, insert -- (SEQ ID No: 40) -- before the period;
Line 24, insert -- (SEQ ID No: 41) -- before the period;
Line 25, insert -- (SEQ ID No: 42) -- before the period;
Line 26, insert -- (SEQ ID No: 43) -- before the period;
Line 27, insert -- partial -- in place of "full" and insert -- (SEQ ID No: 44) -- before the period.

Column 11,
Line 3, replace "full" with -- partial --.

Columns 17 and 18,
Line 37, insert -- Key to sequence annotation -- (a total of 12 pages) as shown on attached pages.

Page 7,
Line 1, of the "Key to sequence annotation", please replace "Complete" with -- Partial --

Column 48,
Delete claim 20.

Signed and Sealed this

Seventeenth Day of December, 2002

JAMES E. ROGAN
*Director of the United States Patent and Trademark Office*

Key to sequence annotation:

| | |
|---|---|
| Lower-case | plasmid backbone sequence |
| *Lower-case italics* | sequence inserted to the pTV00 or pGR107 vectors |
| Lower-case underlined | CaMV 35S promoter sequence |
| UPPER-CASE | tobravirus cDNA sequence |
| *UPPER-CASE ITALICS* | Nopaline synthase terminator sequence |
| UPPER-CASE AND BOLD | Arabidopsis NIA1-intron 3 sequence |
| Lower-case and bold | CaMV35S terminator sequence |

1: pTV00 sequence.

tttttatccccggaagcctgtggatagagggtagttatccacgtgaaaccgctaatgccccgcaaagccttgattcacggggctttccggcccgctccaaaaactatccacgtgaaatcgctaatcagggtacgtgaaatcgctaatcggagtacgtgaaatcgctaataaggtcacgtgaaatcgctaatcaaaaaggcacgtgagaacgctaatagcccttcagatcaacagcttgcaaacacccctcgctccggcaagtagttacagcaagtagtatgttcaattagcttttcaattatgaatatatatatcaattattggtcgcccttggcttgtggacaatgcgctacgcgcaccggctccgcccgtggacaaccgcaagcggttgcccaccgtcgagcgccagcgcctttgcccacaacccggcggccggccgcaacagatcgtttataaatttttttttttgaaaaagaaaaagcccgaaaggcggcaacctctcgggctctctggatttccgatccccggaattagatctcaaacaaacacatacagcgacttagtttacccgccaatatatcctgtcaaggccttcatgttctttcctgcgttatcccctgattctgtggataaccgtattaccgcctttgagtgagctgataccgctcgccgcagccgaacgaccgagcgcagcgagtcagtgagcgaggaagcggaagagcgcccaatacgcaaaccgcctctccccgcgcgttggccgattcattaatgcagctggcacgacaggtttcccgactggaaagcgggcagtgagcgcaacgcaattaatgtgagttagctcactcattaggcaccccaggctttacactttatgcttccggctcgtatgttgtgtggaattgtgagcggataacaatttcacacaggaaacagctatgaccatgattacgccaagctcggaattaaccctcactaaagggaacaaaagctggagctcc<u>accgcggtggagctccaccggggaaacctcctcgggattccattgcccagctatctgtcactttattgagaagatagtggaaaaggaaggtggctcctacaaatgccatcattgcgataaaggaaaggccatcgttgaagatgcctctgccgacagtggtcccaaagatggacccccacccacgaggagcatcgtggaaaaagaagacgttccaaccacgtcttcaaagcaagtggattgatgtgatatctccactgacgtaagggatgacgcacaatcccactatccttcgcaagacccttcctctatataaggaagttcatttcatttggagaggctag</u>ATAAAAC

2

ATTGCACCTATGGTGTTGCCCTGGCTGGGGTATGTCAGTGATCGCAGTAGAA
TGTACTAATTGACAAGTTGGAGAATACGGTAGAACGTCCTTATCCAACACAG
CCTTTATCCCTCTCCCTGACGAGGTTTTGTCAGTGTAATATTTCTTTTTGAAC
TATCCAGCTTAGTACCGTACGGGAAAGTGACTGGTGTGCTTATCTTTGAAAT
GTTACTTTGGGTTTCGGTTCTTTAGGTTAGTAAGAAAGCACTTGTCTTCTCAT
ACAAAGGAAAACCTGACGTATCGCTTACGAAAGTAGCAATGAAAGAAGGT
GGTGGTTTTAATCGTACCGCAAAAACGATGGGGTCGTTTTAATTAACTTCT
CCTACAAGCGTCTAAACGGACGTTGGGGTTTTGCTAGTTTCTTTAGAGAAAA
CTAGCTAAGTCTTTAATGTTATCATTAGAGATGGCATAAATATAATACTTGT
GTCTGCTGATAAGATCATTTTAATTTGGACGATTAGACTTGTTGAACTACAG
GTTACTGAATCACTTGCGCTAATCAACATGGGAGATATGTACGATGAATCAT
TTGACAAGTCGGGCGGTCCTGCTGACTTGATGGACGATTCTTGGGTGGAATC
AGTTTCGTGGAAAGATTTGTTGAAGAAGTTACACAGCATAAAATTTGCACTA
CAGTCTGGTAGAGATGAGATCACTGGGTTACTAGCGGCACTGAATAGACAG
TGTCCTTATTCACCATATGAGCAGTTTCCAGATAAGAAGGTGTATTTCCTTTT
AGACTCACGGGCTAACAGTGCTCTTGGTGTGATTCAGAACGCTTCAGCGTTC
AAGAGACGAGCTGATGAGAAGAATGCAGTGGCGGGTGTTACAAATATTCCT
GCGAATCCAAACACAACGGTTACGACGAACCAAGGGAGTACTACTACTACC
AAGGCGAACACTGGCTCGACTTTGGAAGAAGACTTGTACACTTATTACAAAT
TCGATGATGCCTCTACAGCTTTCCACAAATCTCTAACTTCGTTAGAGAACAT
GGAGTTGAAGAGTTATTACCGAAGGAACTTTGAGAAAGTATTCGGGATTAA
GTTTGGTGGAGCAGCTGCTAGTTCATCTGCACCGCCTCCAGCGAGTGGAGGT
CCGATACGTCCTAATCCCTAGGGATTTAAGGACGTGAACTCTGTTGAGATCC
TAGAactagtggatccccgggctgcaggaattcgatatcaagcttatcgataccgtcgacctcgaggggggggcccggta
cccAATTCGCCCTATAGTGAGTCGTATTACAATTCACTGGCCGTCGTTTTACAA
CGTCGTGACTGGGAAAACCCTGGCGTTACCCAACTTAATCGCCTTGCAGCAC
ATCCCCCTTTCGCCAGCTGGCGTAATAGCGAAGAGGCCCGCACCGATCGCCC

3

TTCCCAACAGTTGCGAAGACATTAAACTACGGTTCTTTAAGTAGATCCGTGC
CTGAAGTTTTAGGTTCAATTTAAACCTACGAGATTGACATTCTCGACTGATCT
TGATTGATCGGTAAGTCTTTTGTAATTTAATTTTCTTTTTGATTTTATTTTAAA
TTGTTATCTGTTTCTGTGTATAGACTGTTTGAGATCGGCGTTTGGCCGACTCA
TTGTCTTACCATAGGGGAACGGACTTTGTTTGTGTTGTTATTTTATTTGTATTT
TATTAAAATTCTCAACGATCTGAAAAAGCCTCGCGGCTAAGAGATTGTTGGG
GGGTGAGTAAGTACTTTTAAAGTGATGATGGTTACAAAGGCAAAAGGGGTA
AAACCCCTCGCCTACGTAAGCGTTATTACGCCCTCGAGTATCGAATTGCTGC
AGGCATGCAAGCGATCCCCGATCGTTCAAACATTTGGCAATAAAGTTTCTTA
AGATTGAATCCTGTTGCCGGTCTTGCGATGATTATCATATAATTTCTGTTGAA
TTACGTTAAGCATGTAATAATTAACATGTAATGCAT*GACGTTATTTATGAGATG*
*GGTTTTTATGATTAGAGTCCCGCAATTATACATTTAATACGCGATAGAAAACAAAAT*
*ATAGCGCGCAAACTAGGATAAATTATCGCGCGGTGTCATCTATGTTACTAGATC*
*GGGAATTGCCAAGCTGCTTGGCACTGGCCGTCGTTTTACAACGTCGTGACTGGGA*
*AAACCCTGGCGTTACCCAACTTAATCGCCTTGCAGCACATCCCCCTTTCGCCAGC*
*TGGCGTAATAGCGAAGAGGCCCGCACCGATCGCCCTTCCCAACAGTTGCGCA*gcct
gaatggcgaatggcgcgaaattgtaaacgttaatgttaacgttacaccacaatatatcctgccaagatctcatgtgagcaaaagg
ccagcaaaaggccaggaaccgtaaaaaggccgcgttgctggcgttttccataggctccgcccccctgacgagcatcacaaa
aatcgacgctcaagtcagaggtggcgaaacccgacaggactataaagataccaggcgtttccccctggaagctccctcgtgc
gctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgcct
tatccggtaactatcgtcttgagtccaacccggtaagacacgacttatcgccactggcagcagccactggtaacaggattagca
gagcgaggtatgtaggcggtgctacagagttcttgaagtggtggcctaactacggctacactagaaggacagtatttggtatct
gcgctctgctgaagccagttaccttcggaaaaagagttggtagctcttgatccggcaaacaaaccaccgctggtagcggtggtt
tttttgtttgcaagcagcagattacgcgcagaaaaaaaggatctcaagaagatcctttgatcttttctacggggtctgacgctcagt
ggaacgaaaactcacgttaagggattttggtcatggttacaaccaattaaccaattctgattagaaaaactcatcgagcatcaaat
gaaactgcaatttattcatatcaggattatcaataccatattttgaaaaagccgtttctgtaatgaaggagaaaactcaccgaggc agttccataggatggcaagatcctggtatcggtctgcgattccgactcgtccaacatcaatacaacctattaatttcccctcgtcaa
aaataaggttatcaagtgagaaatcaccatgagtgacgactgaatccggtgagaatggcaaaagtttatgcatttctttccagact
tgttcaacaggccagccattacgctcgtcatcaaaatcactcgcatcaaccaaaccgttattcattcgtgattgcgcctgagcgag
acgaaatacgcgatcgctgttaaaaggacaattacaaacaggaatcgaatgcaaccggcgcaggaacactgccagcgcatc
aacaatattttcacctgaatcaggatattcttctaatacctggaatgctgttttccctgggatcgcagtggtgagtaaccatgcatca
tcaggagtacggataaaatgcttgatggtcggaagaggcataaattccgtcagccagtttagtctgaccatctcatctgtaacatc
attggcaacgctacctttgccatgtttcagaaacaactctggcgcatcgggcttcccatacaatccatagattgtcgcacctgattg
cccgacattatcgcgagcccatttatacccatataaatcagcatccatgttggaatttaatcgcggcctggagcaagacgtttccc
gttgaatatggctcataacaccccttgtattactgtttatgtaagcagacagttttattgttcatgatgatatattttatcttgtgcaatgt
aacatcagagattttgagacacaacgtggctttgttgaataaatcgaacttttgctgagttgaaggatcagatcacgcatcttcccg
acaacgcagaccgttccgtggcaaagcaaaagttcaaaatcaccaactggtccacctacaacaaagctctcatcaaccgtgct
ccctcactttctggctggatgatggggcgattcaggcgatccccatccaacagcccgccgtcgagcgggct

(2) PEBV coat protein promoter:

GGATCCGCACACAAGGTTAAAAACGCTGTAGTAATACATGCGCAAGAACAG
GCTGAGCATCTTGTTCTGGGGTTTCACACTATCTTTAGAGAAAGTGTTAAGTT
AATTAAGTTATCTTAATTAAGAGCATAATTATACTGATTTGTCTCTCGTTGAT
AGAGTCTATCATTCTGTTCTAAAAATTTGACAACTCGGTTTGCTGACCTACTG
GTTACTGTATCACTTACCCGAGTTAACGAGGGCGCGCCC

(3) *N. benthamiana* pds partial cDNA sequence:

*tctgtcaaaccatatatggacatttatcacaggaactcccactagcttctccaacttttggaaatatgggatctctttccagtctt*
*caggcaaaagaagcttcaagatatccactggagtggcaaacacaaaagcatctcctttaattgtactgccattattctgtata*
*aaacatttgacacttccatcctcattcagctcgatcttttttattcgtgagtttagtctgacttggccaccttttgactcaatatgttc*

*cacaatcggcatgcaaagtctctcaggagggttaccatctaaaaaggccattttttgaaccatgtttctcctgaagaaatctgtt*

*caaagcaatcaagatgcactgcatcgaaagctcgtcagggtttataaagttgagtgcctctagactg*

(4) *A. thaliana* pds partial cDNA sequence:

*ctcgagagatgtcaaatctgtgagattcatttactgaagagagtaaggttaagtttggattgcaatgagatttatacacaaat*

*aataatgcttacaagcaaatcatctttaagttttgtcctcttctcatgatgatgatactgttgcctccgacaactttcttggtccag*

*acgcagccagtagctcgtaatcctgaacaatagactgagagcagaatttgccagagaggacagcgccttccatggaagc*

*taagtacttctgttttgtgtaatctccagctaagtagaatccttcaataggtgatctttgtagaggacgacatggttcacagtttg*

*ggatggtcttgtacacagatcttggagtcttaacgacatggtacttcagaattttagctttgctttggtcagctgagatttcatca*

*gggaagagtttctcaagttctttcattgttgcatctatgatgtcagaatcagtccgtgatatccattcctctgctggtgcaaatact*

*agctccagcattgaccggttaggatcgtaatattccttacaagttaaggacatgtcggcatacacgctcagaaggttacttct*

*gctaaagagtaggtgatcatatgtgttcttcagttttcgatcaaaccatatatgaacattaataactggtactccaactaatttat*

*ccaatttcttgaagtacggtatttctttccagggatctggtaaaaggagcttcaggatatcgactggagcggcaaacacata*

*agcgtctccttcgacagtgcttccattagtgagtaagaaactcttaaccgtgccatcgtcattgagctcaattttctttatcctag*

*aattaagttgcacttccccacctagtgatcgaatatgatccactactggcatacaaagcctttccggaggattaccatccaag*

*aatgccatcttggaaccatgttttcctgaagaaaccggttcaaagctatcaaaatgcattgcattgacagttcatcagggttt*

*ataaagtttagcgcctttgacatggcaataaacacctcgtcggtcacgcgctcaggtactccctgcttttccatccattctttga*

*ctgataaaccatcttgggcctcaacataagcctgaccgccgaccatggctggcaaaagtccaatagcaaactttatttctct*

*ggccatgtcagcatctcgttgttccgcaaaatagcccaaataccatttaagggtgctggtaggacatctgggaagtcaaatc*

*tactaaattctccaggtttacttggcatagcaaaaatcatggagtgttccttccactgcaaccgatcattgatcccaagttctcc*

*aaataaattctgcacattcggataagcaccgaagaaaatatgtaaaccagtctcataccagtccccatcttcatccttccatg*

*cagctatctttccaccaagaacatctcttgcttcaagcaacagaggtttgtggcctgcatcagccaggtactttgcagttgaca*

*atccagccaatccagcaccagcaattacaactttcaaaggcttagcaggacgaggagcactacggaaggatgcagata*

*aactagcagcttccaagaaattgacagtgttctctagctctggccttggaatatccacacaaactacctgcaaaggaccag*

*cagtactcctcctccttgttcttgtcttaagcgcttgagaagtgggaaccctaaagctatgtcccattagttcacaacctccaga*

*tgaaagtgcctcgag*

(5) *N. benthamiana* rubisco partial cDNA sequence;

*agtctagatggcttcctcagttctttcctctgcagcagttgccacccgcagcaatgttgctcaagctaacatggttgcacctttc actggccttaagtcagctgcctcattccctgtttcaaggaagcaaaaccttgacatcacttccattgccagcaacggcggaa gagtgcaatgcatgcaggtgtggccaccaattaacaagaagaagtacgagactctctcataccttcctgatttgagccagg agcaattgcttagtgaagttgagtaccttttgaaaaatggatgggttccttgcttggaattcgagactgagcacggatttgtcta ccgtgaaaacaacaagtcaccaggatactatgatggcagatactggaccatgtggaagctacctatttcggatgcactgat gccacccaagtgttggctgaggtggaagaggcgaagaaggcatacccacaggcctggatccgtatcattggattcgaca acgtgg*

(6) Partial cDNA sequence from the 3' end of GFP

*gatggaaacattcttggacacaaattggaatacaactataactcacacaatgtatacatcatggcagacaaacaaaagaa tggaatcaaagttaacttcaaaattagacacaacattgaagatggaagcgttcaactagcagaccattatcaacaaaata ctccaattggcgatggccctgtccttttaccagacaaccattacctgtccacacaatctgcccttcgaaagatcccaacgaa aagagagaccacatggtccttcttgagtttgtaacagctgctgggattacacatggcatggatgaactatacaaataa*

(7) *N. benthamiana* partial cDNA sequence from NFL

*tggacccagaggctttctcagcgagtttgttcaaatgggaccctagaggtgcaatgccaccgccaacccggctgttggaag ccgcggtggcgcctcctcctccaccaccagttctgccaccgccgcagcctctatcggcggcctattccattaggacaaggg agttaggagggctagaggagttgtttcaagcttacggtatacgttattacactgctgctaaaatagcggagctaggttttacg gtgaatactctattggacatgaaagatgaggaacttgatgatatgatgaatagcctttcacagattttcagatgggaactcct cgtcggagaaaggtacggtatcaaagctgcaatcagggcggaacggcggaggcttgaggaggaagaactacggcgg cgcagccaccttctgtc*

(8) Partial sequence of Pbintra 6 plasmid.

tactccaaaaatgtcaaagatacagtctcagaagaccaaagggctattgagacttttcaacaaagggtaatttcgggaaacctcc
tcggattccattgcccagctatctgtcacttcatcgaaaggacagtagaaaaggaaggtggctcctacaaatgccatcattgcga
taaaggaaaggctatcattcaagatgcctctgccgacagtggtcccaaagatggaccccacccacgaggagcatcgtggaa
aaagaagacgtcccaaccacgtcttcaaagcaagtggattgatgtgacatctccactgacgtaagggatgacgcacaatccca
ctatccttcgcaagacccttcttctatataaggaagttcatttcatttggagaggacagcccaagctttctagagGATCCAT
AAAACATTTCAATCCTTTGAACGCGGTAGAACGTGCTAATTGGATTTTGGTG
AGAACGCGGTAGAACGTACTTATCACCTACAGTTTTATTTTGTTTTTCTTTTT
GGTTTAATCTATCCAGCTTAGTACCGAGTGGGGGAAAGTGACTGGTGTGCCT
AAAACCTTTTCTTTGATACTTTGTAAAAATACATACAGATACAATGGCGAAC
GGTAACTTCAAGTTGTCTCAATTGCTCAATGTGGACGAGATGTCTGCTGAGC
AGAGGAGTCATTTCTTTGACTTGATGCTGACTAAACCTGATTGTGAGATCGG
GCAAATGATGCAAAGAGTTGTTGTTGATAAAGTCGATGACATGATTAGAGA
AAGAAAGACTAAAGATCCAGTGATTGTTCATGAAGTTCTTTCTCAGAAGGAA
CAGAACAAGTTGATGGAAATTTATCCTGAATTCAATATCGTGTTTAAAGACG
ACAAAAACATGGTTCATGGGTTTGCGGCTGCTGAGCGAAAACTACAAGCTTT
ATTGCTTTTAGATAGAGTTCCTGCTCTGCAAGAGGTGGATGACATCGGTGGT
CAATGGTCGTTTTGGGTAACTAGAGGTGAGAAAAGGATTCATTCCTGTTGTC
CAAATCTAGATATTCGGGATGATCAGAGAGAAATTTCTCGACAGATATTTCT
TACTGCTATTGGTGATCAAGCTAGAAGTGGTAAGAGACAGATGTCGGAGAA
TGAGCTGTGGATGTATGACCAATTTCGTGAAAATATTGCTGCGCCTAACGCG
GTTAGGTGCAATAATACATATCAGGGTTGTACATGTAGGGGTTTTTCTGATG
GTAAGAAGAAAGGCGCGCAGTATGCGATAGCTCTTCACAGCCTGTATGACTT
CAAGTTGAAAGACTTGATGGCTACTATGGTTGAGAAGAAAACTAAAGTGGT
TCATGCTGCTATGCTTTTTGCTCCTGAAAGTATGTTAGTGGACGAAGGTCCAT
TACCTTCTGTTGACGGTTACTACATGAAGAAGAACGGGAAGATCTATTTCGG
TTTTGAGAAAGATCCTTCCTTTTCTTACATTCATGACTGGGAAGAGTACAAG

8

AAGTATCTACTGGGGAAGCCAGTGAGTTACCAAGGGAATGTGTTCTACTTCG
AACCGTGGCAGGTGAGAGGAGACACAATGCTTTTTTCGATCTACAGGATAG
CTGGAGTTCCGAGGAGGTCTCTATCATCGCAAGAGTACTACCGAAGAATATA
TATCAGTAGATGGGAAAGCATGGTTGTTGTCCCAATTTTCGATCTGGTCGAA
TCAACGCGAGAGTTGGTCAAGAAAGACCTGTTTGTAGAGAAACAATTCATG
GACAAGTGTTTGGATTACATAGCTAGGTTATCTGACCAGCAGCTGACCATAA
GCAATGTTAAATCATACTTGAGTTCAAATAATTGGGTCTTATTCATAAACGG
GGCGGCCGTGAAGAACAAGCAAAGTGTAGATTCTCGAGATTTACAGTTGTT
GGCTCAAACTTTGCTAGTGAAGGAACAAGTGGCGAGACCTGTCATGAGGGA
GTTGCGTGAAGCAATTCTGACTGAGACGAAACCTATCACGTCATTGACTGAT
GTGCTGGGTTTAATATCAAGAAACTGTGGAAGCAGTTTGCTAACAAGATCG
CAGTCGGCGGATTCGTTGGCATGGTTGGTACTCTAATTGGATTCTATCCAAA
GAAGGTACTAACCTGGGCGAAGGACACACCAAATGGTCCAGAACTATGTTA
CGAGAACTCGCACAAAACCAAGGTGATAGTATTTCTGAGTGTTGTGTATGCC
ATTGGAGGAATCACGCTTATGCGTCGAGACATCCGAGATGGACTGGTGAAA
AAACTATGTGATATGTTTGATATCAAACGGGGGGCCCATGTCTTAGACGTTG
AGAATCCGTGCCGCTATTATGAAATCAACGATTTCTTTAGCAGTCTGTATTC
GGCATCTGAGTCCGGTGAGACCGTTTTACCAGATTTATCCGAGGTAAAAGCC
AAGTCTGATAAGCTATTGCAGCAGAAGAAAGAAATCGCTGACGAGTTTCTA
AGTGCAAAATTCTCTAACTATTCTGGCAGTTCGGTGAGAACTTCTCCACCAT
CGGTGGTCGGTTCATCTCGAAGCGGACTGGGTCTGTTGTTGGAAGACAGTAA
CGTGCTGACCCAAGCTAGAGTTGGAGTTTCAAGAAAGGTAGACGATGAGGA
GATCATGGAGCAGTTTCTGAGTGGTCTTATTGACACTGAAGCAGAAATTGAC
GAGGTTGTTTCAGCCTTTTCAGCTGAATGTGAAAGAGGGGAAACAAGCGGT
ACAAAGGTGTTGTGTAAACCTTTAACGCCACCAGGATTTGAGAACGTGTTGC
CAGCTGTCAAACCTTTGGTCAGCAAAGGAAAAACGGTCAAACGTGTCGATT
ACTTCCAAGTGATGGGAGGTGAGAGATTACCAAAAAGGCCGGTTGTCAGTG

9

GAGACGATTCTGTGGACGCTAGAAGAGAGTTTCTGTACTACTTAGATGCGGA
GAGAGTCGCTCAAAATGATGAAATTATGTCTCTGTATCGTGACTATTCGAGA
GGAGTTATTCGAACTGGAGGTCAGAATTACCCGCACGGACTGGGAGTGTGG
GATGTGGAGATGAAGAACTGGTGCATACGTCCAGTGGTCACTGAACATGCTT
ATGTGTTCCAACCAGACAAACGTATGGATGATTGGTCGGGATACTTAGAAGT
GGCTGTTTGGGAACGAGGTATGTTGGTCAACGACTTCGCGGTCGAAAGGAT
GAGTGATTATGTCATAGTTTGCGATCAGACGTATCTTTGCAATAACAGGTAA
TAATCCTCTCTCTTGATATTTTAAATTATAGAATTAATTAGTTTACTTTA
TTCTTTACTATATGATTTAAATAGTTTAATCTTGTTTTTGAGTAAACTAT
TCGATTTTGATATTTGTATTCGTCCTACAAAGTTGGAAATACTGATGATA
TTTTCTTTTGAACGTGATACCTACCAATACTAATCTTACGGAATCTTTTA
ATAGAGCACTAATCAACATGGAACTAAAGACCAATTCTTAAGTGTCTCT
GTTGTACAGTTCATTTTAGTAGTGCGTTTAAGTATTATTATCTCCCTTCA
TGCGGGGCAATTATGTAGATTAAAATCGAATTATATAAAATTTACATA
AGTCTAAGTCTAGGGTCTCCAGCTAATTGTTATTTTTTAACGATGTTGA
CTAAAGCAATAACGACGTTGACTTGTGTTAAACAGGTTGATCTTGGACAA
TTTAAGTGCCCTGGATCTAGGACCAGTTAACTGTTCTTTTGAATTAGTTGACG
GTGTACCTGGTTGTGGTAAGTCGACAATGATTGTCAACTCAGCTAATCCTTG
TGTCGATGTGGTTCTCTCTACTGGGAGAGCAGCAACCGACGACTTGATCGAG
AGATTCGCGAGCAAAGGTTTTCCATGCAAATTGAAAAGGAGAGTGAAGACG
GTTGATTCTTTTTGATGCATTGTGTCGATGGTTCTTTAACCGGAGACGTGTT
GCATTTCGACGAAGCTCTCATGGCCCATGCTGGTATGGTGTACTTTGCGCTC
AGATAGCTGGTGCTAAACGATGTATCTGTCAAGGAGATCAGAATCAAATTTC
TTTCAAGCCTAGGGTATCTCAAGTTGATTTGAGGTTTTCTAGTCTGGTCGGAA
AGTTTGACATTGTTACAGAAAAAGAGAAACTTACAGAAGTCCAGCAGATG
TGGCTGCCGTATTGAACAAGTACTATACTGGAGATGTCAGAACACATAACGC
GACTGCTAATTCGATGACGGTGAGGAAGATTGTGTCTAAAGAACAGGTTTCT

10

TTGAAGCCTGGTGCTCAGTACATAACTTTCCTTCAGTCTGAGAAGAAGGAGT
TGGTAAATTTGTTGGCATTGAGGAAAGTGGCAGCTAAAGTGAGTACAGTAC
ACGAGTCGCAAGGAGAGACATTCAAAGATGTAGTCCTAGTCAGGACGAAAC
CTACGGATGACTCAATCGCTAGAGGTCGGGAGTACTTAATCGTGGCATTGTC
GCGTCACACACAATCACTTGTGTATGAAACTGTGAAAGAGGACGATGTAAG
CAAAGAGATCAGGGAAAGTGCCGCGCTTACGAAGGCGGCTTTGGCAAGATT
TTTTGTTACTGAGACCGTCTTATGACGGTTTCGGTCTAGGTTTGATGTCTTTA
GACATCATGAAGGGCCTTGCGCCGTTCCAGATTCAGGTACGATTACGGACTT
GGAGATGTGGTACGACGCTTTGTTTCCGGGAAATTCGTTAAGAGACTCAAGC
CTAGACGGGTATTTGGTGGCAACGACTGATTGCAATTTGCGATTAGACAATG
TTACGATCAAAAGTGGAAACTGGAAAGACAAGTTTGCTGAAAAGAAACGT
TTCTGAAACCGGTTATTCGTACTGCTATGCCTGACAAAGGAAGACTACTCA
GTTGGAGAGTTTGTTAGCATTGCAGAAAAGGAACCAAGCGGCACCCGATCT
ACAAGAAAATGTGCACGCGACAGTTCTAATCGAAGAGACGATGAAGAAGCT
GAAATCTGTTGTCTACGATGTGGGAAAAATTCGGGCTGATCCTATTGTCAAT
AGAGCTCAAATGGAGAGATGGTGGAGAAATCAAAGCACAGCGGTACAGGCT
AAGGTAGTAGCAGATGTGAGAGAGTTACATGAAATAGACTATTCGTCTTAC
ATGTATATGATCAAATCTGACGTGAAACCTAAGACTGATTTAACACCGCAAT
TTGAATACTCAGCTCTACAGACTGTTGTGTATCACGAGAAGTTGATCAACTC
GTTGTTCGGTCCAATTTTCAAAGAAATTAATGAACGCAAGTTGGATGCTATG
CAACCACATTTTGTGTTCAACACGAGAATGACATCGAGTGATTTAAACGATC
GAGTGAAGTTCTTAAATACGGAAGCGGCTTACGACTTTGTTGAGATAGACAT
GTCTAAATTCGACAAGTCGGCAAATCGCTTCCATTTACAACTGCAGCTGGAG
ATTTACAGGTTATTTGGGCTGGATGAGTGGGCGGCCTTCCTTTGGGAGGTGT
CGCACACTCAAACTACTGTGAGAGATATTCAAAATGGTATGATGGCGCATAT
TTGGTACCAACAAAGAGTGGAGATGCTGATACTTATAATGCAAATTCAGAT
AGAACACTGTGTGCACTCTTGTCTGAATTACCATTGGAGAAAGCAGTCATGG

11

TTACATATGGAGGAGATGACTCACTGATTGCGTTTCCTAGAGGAACGCAGTT
TGTTGATCCGTGTCCAAAGTTGGCTACTAAGTGGAATTTCGAGTGCAAGATT
TTTAAGTACGATGTCCCAATGTTTTGTGGGAAGTTCTTGCTTAAGACGTCATC
GTGTTACGAGTTCGTGCCAGATCCGGTAAAAGTTCTGACGAAGTTGGGGAA
AAAGAGTATAAAGGATGTGCAACATTTAGCCGAGATCTACATCTCGCTGAAT
GATTCCAATAGAGCTCTTGGGAACTACATGGTGGTATCCAAACTGTCCGAGT
CTGTTTCAGACCGGTATTTGTACAAAGGTGATTCTGTTCATGCGCTTTGTGCG
CTATGGAAGCATATTAAGAGTTTTACAGCTCTGTGTACATTATTCCGAGACG
AAAACGATAAGGAATTGAACCCGGCTAAGGTTGATTGGAAGAAGGCACAGA
GAGCTGTGTCAAACTTTTACGACTGGTAATATGGAAGACAAGTCATTGGTCA
CCTTGAAGAAGAAGACTTTCGAAGTCTCAAAATTCTCAAATCTAGGGGCCAT
TGAATTGTTTGTGGACGGTAGGAGGAAGAGACCGAAGTATTTTCACAGAAG
AAGAGAAACTGTCCTAAATCATGTTGGTGGGAAGAAGAGTGAACACAAGTT
AGACGTTTTTGACCAAAGGGATTACAAAATGATTAAATCTTACGCGTTTCTA
AAGGTAGTAGGTGTACAACTAGTTGTAACATCACATCTACCTGCAGATACGC
CTGGGTTCATTCAAATCGATCTGTTGGATTCGAGACTTACTGAGAAAAGAAA
GAGAGGAAAGACTATTCAGAGATTCAAAGCTCGAGCTTGCGATAACTGTTC
AGTTGCGCAGTACAAGGTTGAATACAGTATTTCCACACAGGAGAACGTACTT
GATGTCTGGAAGGTGGGTTGTATTTCTGAGGGCGTTCCGGTCTGTGACGGTA
CATACCCTTTCAGTATCGAAGTGTCGCTAATATGGGTTGCTACTGATTCGACT
AGGCGCCTCAATGTGGAAGAACTGAACAGTTCGGATTACATTGAAGGCGAT
TTTACCGATCAAGAGGTTTTCGGTGAGTTCATGTCTTTGAAACAAGTGGAGA
TGAAGACGATTGAGGCGAAGTACGATGGTCCTTACAGACCAGCTACTACTA
GACCTAAGTCATTATTGTCAAGTGAAGATGTTAAGAGAGCGTCTAATAAGA
AAAACTCGTCTTAATGCATAAAGAAATTTATTGTCAATATGACGTGTGTACT
CAAGGGTTGTGTGAATGAAGTCACTGTTCTTGGTCACGAGACGTGTAGTATC
GGTCATGCTAACAAATTGCGAAAGCAAGTTGCTGACATGGTTGGTGTCACAC

GTAGGTGTGCGGAAAATAATTGTGGATGGTTTGTCTGTGTTGTTATCAATGA
TTTTACTTTTGATGTGTATAATTGTTGTGGCCGTAGTCACCTTGAAAAGTGTC
GTAAACGTGTTGAAACAAGAAATCGAGAAATTTGGAAACAAATTCGACGAA
ATCAAGCTGAAAACATGTCTGCGACAGCTAAAAAGTCTCATAATTCGAAGA
CCTCTAAGAAGAAATTCAAAGAGGACAGAGAATTTGGGACACCAAAAAGAT
TTTTAAGAGATGATGTTCCTTTCGGGATTGATCGTTTGTTTGCTTTTTGATTTT
ATTTTATATTGTTATCTGTTTCTGTGTATAGACTGTTTGAGATTGGCGCTTGG
CCGACTCATTGTCTTACCATAGGGGAACGGACTTTGTTTGTGTTGTTATTTTA
TTTGTATTTTATTAAAATTCTCAATGATCTGAAAAGGCCTCGAGGCTAAGAG
ATTATTGGGGGGTGAGTAAGTACTTTTAAAGTGATGATGGTTACAAAGGCAA
AAGGGGTAAAACCCCTCGCCTACGTAAGCGTTATTACGCCCgatccccgggagc
tcgaattcgctgaaatcaccagtctctctctacaaatctatctctctctattttttccataaataatgtgtgagtagtttcccgataa
gggaaattagggttcttataggggtttcgctcatgtgttgagcatataagaaaccccttagtatgtatttgtatttgtaaaata
cttctattatcaataaaatttctaattcctaaaaccaaaatccagtactaaaatccagatctcctaaagtccctatagatct
ttgtcgtgaatataaaccagacacgagacgactaaacctggagcccagacgccgttcgaagctagaagtaccgcttag
gcaggaggccgttagggaaaagatgctaaggcagggttggttacgttgactcccccgtaggtttggtttaaatatgatg
aagtggacggaaggaaggaggaagacaaggaaggataaggttgcaggccctgtgcaaggtaagaagatggaaatt
tgatagaggtacgctactatacttatactatacgctaagggaatgcttgtatttataccctataccccctaataaccccctta
tcaatttaagaaataatccgcataagcccccgcttaaaaattggtatcagagccatgaataggtctatgaccaaaactc
aagaggataaaacctcaccaaaatacgaaagagttcttaactctaaagataaaagatctttcaagatcaaaactagtt
ccctcacaccggagcatgcgatatcctcgacctgcaggcatgcaagcttggcgtaatcatggtcatagctgtttcctgtgtgaaa
ttgttatccgctcacaattccacacaacatacgagccggaagcataaagtgtaaagcctggggtgcctaatgagtgagctaact
cacattaattgcgttgcgctcactgcccgctttccagtcgggaaacctgtcgtgccagctgcattaatgaatcggccaacgcgcg
gggagaggcggtttgcgtattgggccaaagacaaaagggcgacattcaaccgattgagggagggaaggtaaatattgacgg
aaattattcattaaaggtgaattatcaccgtcaccgacttgagccatttgggaattagagccagcaaaatcaccagtagcaccatt
accattagcaaggccggaaacgtcaccaatgaaaccatcgatagcagcaccgtaatcagtagcgacagaatcaagtttgcctttt
agcgtcagactgtagcgcgttttcatcggcattttcggtcatagccccttattagcgtttgccatcttttcataatcaaaatcaccg